(12) United States Patent
Schmees et al.

(10) Patent No.: US 7,112,584 B2
(45) Date of Patent: Sep. 26, 2006

(54) NONSTEROIDAL ANTIINFLAMMATORY AGENTS

(75) Inventors: Norbert Schmees, Berlin (DE); Manfred Lehmann, Berlin (DE); Hartmut Rehwinkel, Berlin (DE); Peter Strehlke, Berlin (DE); Stefan Jaroch, Berlin (DE); Heike Schaecke, Berlin (DE); Amdt J. G Schottelius, Belvedere, CA (US)

(73) Assignee: Schering AG, Berlin (DE)

( * ) Notice: Subject to any disclaimer, the term of this patent is extended or adjusted under 35 U.S.C. 154(b) by 0 days.

(21) Appl. No.: 10/739,407

(22) Filed: Dec. 19, 2003

(65) Prior Publication Data
US 2004/0209875 A1   Oct. 21, 2004

Related U.S. Application Data

(60) Provisional application No. 60/438,518, filed on Jan. 8, 2003.

(30) Foreign Application Priority Data
Dec. 20, 2002 (DE) .................... 102 61 874

(51) Int. Cl.
C07D 413/12 (2006.01)
C07D 413/14 (2006.01)
A61K 31/536 (2006.01)
A61P 19/02 (2006.01)

(52) U.S. Cl. .................... 514/230.5; 544/63

(58) Field of Classification Search .................. 544/63; 514/230.5
See application file for complete search history.

(56) References Cited

U.S. PATENT DOCUMENTS 6,245,804 B1 * 6/2001 Lehmann et al. ............ 514/443
6,323,199 B1 * 11/2001 Lehmann et al. ......... 514/230.5
6,344,454 B1 * 2/2002 Lehmann et al. ......... 514/230.5

OTHER PUBLICATIONS

Necela et al. (Proceedings of the American Thoracic Society vol. 1, 2004, pp. 240-246.*
Thomas A. Godwin (Gastrointestinal Diseases, <http://edcenter.med.cornell.edu/CUMC_PathNotes/Gastrointestinal/Gastrointestinal.html>, 51 pages) downloaded on Nov. 8, 2005.*

* cited by examiner

*Primary Examiner*—Kahsay Habte
(74) *Attorney, Agent, or Firm*—Millen, White, Zelano, Branigan, P.C.

(57) ABSTRACT

The invention relates to compounds of general formula I

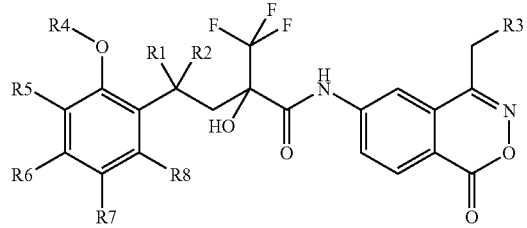

and their use for the production of pharmaceutical agents for treatment and prophylaxis of diseases that coincide with inflammatory, allergic and/or proliferative processes.

19 Claims, No Drawings

NONSTEROIDAL ANTIINFLAMMATORY AGENTS

This application claims the benefit of the filing date of U.S. Provisional Application Ser. No. 60/438,518 filed Jan. 8, 2003.

This invention relates to nonsteroidal compounds and the use of nonsteroidal compounds for the production of pharmaceutical agents for treatment of inflammations.

In addition to a large number of steroid compounds, which bind well to the glucocorticoid receptor and have an antiinflammatory action (glucocorticoids), nonsteroidal compounds are known that namely bind to the glucocorticoid receptor, for which to date no antiinflammatory action has been shown, however [cf. Nature Medicin [Nature Medicine] 4 (1998) 92, Mol. Pharmacol. 52 (1997) 571]. In addition, nonsteroidal compounds were described that are derived from steroidal compounds, have an affinity to the glucocorticoid receptor and probably have an antiinflammatory action that is mediated by the receptor [J. Med. Chem. 36, (1993), 3278–3285]. In animal experiments, however, these compounds did not show any advantages relative to steroidal glucocorticoids, i.e., it was not possible to separate the antiinflammatory action from the metabolic effects, e.g., suppression of the suprarenal function.

From WO 00/32584, phenol derivatives that have a dissociation of action between antiinflammatory action and undesirable metabolic side effects are known as nonsteroidal antiinflammatory agents.

The compounds that are disclosed in the prior art are still in need of improvement with respect to their antiinflammatory active strength and their dissociation of action between antiinflammatory action and the undesirable side effects.

The object was therefore to make available new nonsteroidal antiinflammatory agents that show a better dissociation of action than the compounds of the prior art with at least comparable if not improved active strength.

The compounds that were found are a selection from WO 00/32584.

Nonsteroidal compounds have now been found that bind well to the glucocorticoid receptor and, mediated by this bond, produce an antiinflammatory action. In the experiment, these compounds show a significantly better or at least equally good dissociation of action between antiinflammatory and undesirable actions and are superior to the previously described nonsteroidal glucocorticoids or have at least just as good an action.

According to this invention, suitable compounds for the production of pharmaceutical agents that have an antiinflammatory action are the nonsteroidal compounds of general formula I,

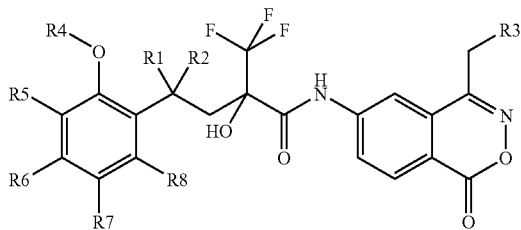

in which
$R^1$ and $R^2$ are the same or different and stand for a $C_1$–$C_2$-alkyl group, or, together with the C atom of the chain, stand for a ring with a total of 3–4 links,
$R^3$ stands for a hydrogen atom or a $C_1$–$C_2$-alkyl group,
$R^4$ means a hydrogen atom or a $C_1$–$C_2$-alkyl group,
$R^5$ to $R^8$ are the same or different from one another and are selected from hydrogen or halogen atoms,
  and R4 and R5 together mean a 5-membered heterocyclic ring that in addition to the oxygen atom optionally can contain another oxygen or nitrogen atom, as well as pure enantiomers and racemates thereof.

The compounds of general formula I according to the invention can be present as different stereoisomers because of the presence of asymmetry centers. Both the racemates and the separately present stereoisomers are part of the subject matter of this invention. The (+)-enantiomers are preferred.

From WO 98/54159, a compound is known that is very similar to the compounds that are mentioned here but shows very pronounced action as gestagen. The absolute configuration of this compound could be determined by x-ray structural analysis with (R). Because of the high binding similarity of these substances from WO 98/54159 and the compounds that are present here, the (R) configuration is also assumed for the (+)-enantiomers that are present here.

The substituents that are defined as groups in the compounds of general formula I can have the meanings below in each case.

The $C_1$–$C_2$-alkyl groups can readily be a methyl or ethyl group.

A fluorine, chlorine, bromine or iodine atom can stand for a halogen atom.

If $R^1$ and $R^2$ together with the C atom of the chain form a 3- to 4-membered ring, the latter is a cyclopropyl ring or a cyclobutyl ring.

If $R^4$ and $R^5$ form a common ring, then the 1,3-dioxole, furanyl, dihydrofuranyl and 1,3-oxazole ring systems are especially preferred.

Substituents $R^4$ to $R^8$, independently of one another, can mean hydrogen atoms or halogen atoms or together form a ring, as described above. The aromatic nature of the phenyl ring stays the same.

The racemic mixtures that are mentioned in the invention can be separated into the pure, optically active forms according to the methods of racemate separation that are familiar to one skilled in the art. For example, the racemic mixtures can be separated into the pure isomers by chromatography on an even optically active carrier material (CHIRALPAK AD®). It is also possible to esterify the free hydroxy group in a racemic compound of general formula I with an optically active acid and to separate the diastereoisomeric esters that are obtained by fractionated crystallization or by chromatography and to saponify the separated esters in each case to form the optically pure isomers. As an optically active acid, for example, mandelic acid, camphorsulfonic acid or tartaric acid can be used.

Preferred according to this invention are those compounds of general formula I, in which:
  $R^1$ and $R^2$ are the same or different and stand for a methyl or ethyl group, and also together with the C atom of the chain, $R^1$ and $R^2$ stand for a cyclopropyl ring or a cyclobutyl ring, and/or
  $R^3$ is a hydrogen atom or a methyl group, and/or
  $R^4$ means a hydrogen atom or a methyl group, and/or
  $R^5$ to $R^8$ mean a hydrogen atom and optionally fluorine, chlorine, bromine or iodine atoms in one or two positions, and/or $R^4$ and $R^5$ together with the inclusion of the phenyl ring atoms 2 and 3 stand for a furan ring, a dihydrofuran ring, a 1,3-dioxole ring or a 1,3-oxazole ring, and $R^6$, $R^7$ and $R^8$ stand for a hydrogen atom or for a fluorine, chlorine, bromine or iodine atom optionally in one or two positions, as well as pure enantiomers and racemates thereof.

Especially preferred are the compounds of formula I

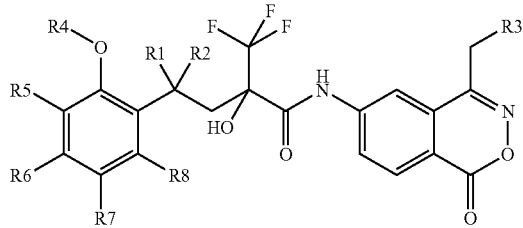

with the meanings of the radicals that are cited in Table 1 below; the isomers for this embodiment can be ignored; it comprises all isomeric forms as well as racemates thereof:

TABLE 1

| Ex. | $R^1/R^2$ | $R^4$–$R^8$(≠H) | $R^3$ | Isomerism** |
|---|---|---|---|---|
| 1 | $CH_3$, $CH_3$ | R4–R5 = —$CH_2$—O— | H | Racemate |
| 2 | $CH_3$, $CH_3$ | R4–R5 = —$CH_2$—O— | H | (+)-Enantiomer |
| 3 | —$(CH_2)_2$— | R4–R5 = —$CH_2$—O— | H | Racemate |
| 4 | —$(CH_2)_2$— | R4–R5 = —$CH_2$—O— | H | (+)-Enantiomer |
| 5 | —$(CH_2)_3$— | R4–R5 = —$CH_2$—O— | H | Racemate |
| 6 | —$(CH_2)_3$— | R4–R5 = —$CH_2$—O— | H | (+)-Enantiomer |
| 7 | $CH_3$, $CH_3$ | R4 = $CH_3$, R7 = Br | H | (+)-Enantiomer |
| 8 | $CH_3$, $CH_3$ | R4–R5 = —CH═CH— | $CH_3$ | (+)-Enantiomer |
| 9 | $CH_3$, $CH_3$ | R4–R5 = —CH═N—, R6 = F | H | (+)-Enantiomer |
| 10 | —$(CH_2)_2$— | R4 = $CH_3$, R5 = F | H | (+)-Enantiomer |
| 11 | $CH_3$, $CH_3$ | R4–R5 = —$CH_2$—O— | $CH_3$ | (+)-Enantiomer |
| 12 | —$(CH_2)_2$— | R4–R5 = —$CH_2$—$CH_2$— | H | Racemate |
| 13 | —$(CH_2)_2$— | R4–R5 = —$CH_2$—$CH_2$— | H | (+)-Enantiomer |
| 14 | —$(CH_2)_3$— | R4–R5 = —$CH_2$—$CH_2$— | H | Racemate |
| 15 | —$(CH_2)_3$— | R4–R5 = —$CH_2$—$CH_2$— | H | (+)-Enantiomer |
| 16 | —$(CH_2)_3$— | R4–R5 = —$CH_2$—$CH_2$— | $CH_3$ | Racemate |
| 17 | —$(CH_2)_3$— | R4–R5 = —$CH_2$—$CH_2$— | $CH_3$ | (+)-Enantiomer |
| 18 | $CH_3$, $CH_3$ | R7 = F, R4–R5 = —$CH_2$—O— | H | Racemate |
| 19 | $CH_3$, $CH_3$ | R7 = F, R4–R5 = —$CH_2$—O— | H | (+)-Enantiomer |
| 20 | $CH_3$, $CH_3$ | R6 = Br, R4–R5 = —$CH_2$—O— | H | (+)-Enantiomer |
| 21 | —$(CH_2)_2$— | R4 = $CH_3$, R6 = I | H | (+)-Enantiomer |
| 22 | $CH_3$, $CH_3$ | R5 = R7 = F | H | (+)-Enantiomer |
| 23 | $CH_3$, $CH_3$ | R4–R5 = —CH═CH— | H | (+)-Enantiomer |
| 24 | $(CH_2)_3$ | R4–R5 = —CH═CH— | H | (+)-Enantiomer |
| 25 | —$(CH_2)_2$— |  | H | (+)-Enantiomer |
| 26 | —$(CH_2)_3$— | R4–R5 = —CH═N—, R6 = F | H | Racemate |
| 27 | —$(CH_2)_3$— | R4–R5 = —CH═N—, R6 = F | H | (+)-Enantiomer |
| 28 | —$(CH_2)_3$— | R7 = F | H | Racemate |
| 29 | —$(CH_2)_3$— | R7 = F | H | (+)-Enantiomer |
| 30 | —$(CH_2)_2$— | R5 = F | H | (+)-Enantiomer |
| 31 | —$(CH_2)_3$— | R4 = $CH_3$, R5 = F | H | Racemate |
| 32 | —$(CH_2)_3$— | R4 = $CH_3$, R5 = F | H | (+)-Enantiomer |
| 33 | —$(CH_2)_3$— | R5 = F | H | (+)-Enantiomer |
| 34 | $CH_3$, $CH_3$ | R5 = F | H | (+)-Enantiomer |
| 35 | $CH_3$, $CH_2CH_3$ | R5 = F | H | (+)-Enantiomer |

The table can be read as follows:

In column $R^4$-$R^8$ (≠H), only the radicals that do not mean hydrogen are presented in one line. Any radicals $R^4$ to $R^8$ that are not otherwise indicated mean hydrogen.

Another embodiment of this invention specifically comprises the compounds of formula I that are presented in Table 1, taking into consideration their indicated stereochemistry.

The binding of substances to the glucocorticoid receptor (GR) is examined with the aid of a recombinantly produced receptor. Cytosol preparations of Sf9 cells, which had been infected with recombinant baculoviruses, which code for the GR, are used for the binding studies. In comparison to the reference substance [$^3$H]-dexamethasone, the substances show a high to very high affinity to the GR.

In addition, these compounds in the mineral corticoid receptor (MR)-binding test with use of cytosol preparations that consist of Sf9 cells, which had been infected with baculoviruses that code for the MR, and with use of [$^3$H]-aldosterone as a reference substance, show affinities to the MR.

As an essential molecular mechanism for the antiinflammatory action of glucocorticoids, the GR-mediated inhibition of the transcription of cytokines, adhesion molecules, enzymes and other pro-inflammatory factors can be seen. This inhibition is produced by an interaction of the GR with other transcription factors, e.g., AP-1 and NF-kappa-B (for a survey, see Cato, A. C. B. and Wade, E., BioEssays 18, 371–378, 1996).

The compounds of general formula I according to the invention inhibit the secretion of the cytokine IL-8 that is triggered by lipopolysaccharide (LPS) in human monocyte cell line THP-1. The concentration of the cytokines was determined in the supernatant with use of commercially available ELISA kits.

The compounds of formula I are distinguished by their ability to respond to the transrepression mechanism more strongly via the GR (lower power) than to the transactivation mechanism. This was measured via the determination of transactivation and transrepression with the aid of the reporter gene test in human HeLa cells. The MMTV promoter (transactivation) and the IL-6 promoter (transrepression) in each case were upstream to the gene that codes for the luciferase. By means of the photometric determination of the enzyme activity of the luciferase, it was possible to measure the activation of the transcription (MMTV-promoter-construct) or the inhibition of the transcription (IL-6-promoter-construct) by the GR.

The antiinflammatory actions of the compounds of general formula I were tested in the animal experiment by tests in the croton oil-induced inflammation in rats and mice (J. Exp. Med. (1995), 182, 99–108). In this connection, croton oil in ethanolic solution was administered topically to the animals' ears. The test substances were also administered topically or systemically simultaneously with or two hours before the croton oil. After 16–24 hours, the ear weight was measured as a yardstick of the inflammatory edema, the peroxidase activity was measured as a yardstick of the invasions of granuloctyes, and the elastase activity was measured as a yardstick of the invasion of neutrophilic granuloctyes. In this test, the compounds of general formula I inhibit the three above-mentioned inflammation parameters both after topical administration and after systemic administration.

One of the most frequent undesirable effects of a glucocorticoid therapy is the so-called "steroid diabetes" [cf. Hatz, H. J., Glucocorticoide: Immunologische Grundlagen, Pharmakologie und Therapierichtlinien [Glucocorticoids: Immunological Bases, Pharmacology and Therapy Guidelines], Wissenschaftliche Verlagsgesellschaft mbH, Stuttgart, 1998]. The reason for this is the stimulation of the gluconeogenesis in the liver by induction of the enzymes that are responsible for this effect and by free amino acids, which develop from the degradation of proteins (catabolic action of glucocorticoids). A key enzyme of the catabolic metabolism in the liver is the tyrosinamino transferase (TAT). The activity of this enzyme can be determined photometrically from liver homogenates and represents a good yardstick of the undesirable metabolic actions of the glucocorticoids. To measure the TAT induction, the animals are sacrificed 8 hours after the test substances are administered, the livers are removed, and the TAT activity in the homogenate is measured. In this test, at doses at which they have an antiinflammatory action, the compounds of general formula I do not induce the tyrosinamino transferase, or induce it only to a small extent.

In summary, the new compounds of general formula I compared to the previously used steroidal glucocorticoids have the following properties:

Nonsteroidal structure (i.e., the substances are also effective in patients who, because of an allergic reaction to the basic steroid structures of conventional glucocorticoids, can no longer access the latter for therapy (cf. Lutz, M. E., el-Azhary R. A., Mayo Clin. Proc. 72, 1141–1144, 1997).

similar good antiinflammatory action with little metabolic action better dissociation with at least equally good action with respect to the prior art.

Because of their antiinflammatory and additional antiallergic, immunosuppressive and antiproliferative actions, the compounds of general formula I according to the invention can be used as medications for treatment or prophylaxis of the following pathologic conditions in mammals and humans: In this case, the term "DISEASE" stands for the following indications:

(i) Lung diseases, which coincide with inflammatory, allergic and/or proliferative processes:
  Chronically obstructive lung diseases of any origin, mainly bronchial asthma
  bronchitis of different origins
  all forms of restrictive lung diseases, mainly allergic alveolitis,
  all forms of pulmonary edema, mainly toxic pulmonary edema
  sarcoidoses and granulomatoses, especially Boeck's disease (ii) Rheumatic diseases/auto-immune diseases/degenerative joint diseases, which coincide with inflammatory, allergic and/or proliferative processes
  All forms of rheumatic diseases, especially rheumatoid arthritis, acute rheumatic fever, polymyalgia rheumatica,
  reactive arthritis
  inflammatory soft-tissue diseases of other origins
  arthritic symptoms in degenerative joint diseases (arthroses)
  traumatic arthritides
  collagen diseases of other origins, e.g., systemic lupus erythematodes, scleroderma, polymyositis, dermatomyositis, Sjögren's syndrome, Still syndrome, Felty's syndrome (iii) Allergies which coincide with inflammatory and/or proliferative processes:
  All forms of allergic reactions, e.g., Quincke's edema, hay fever, insect bites, allergic reactions to pharmaceutical agents, blood derivatives, contrast media, etc., anaphylactic shock, urticaria, contact dermatitis (iv) Vascular inflammations (Vasculitis)
  Panarteritis nodosa, temporal arteritis, erythema nodosum (v) Dermatological diseases which coincide with inflammatory allergic and/or proliferative processes:
  Atopic dermatitis (mainly in children)
  psoriasis
  pityriasis rubra pilaris
  erythematous diseases, triggered by different noxae, e.g., radiation, chemicals, burns, etc.
  bullous dermatoses
  diseases of the lichenoid group
  itching (e.g., of allergic origins)
  seborrheal eczema
  rosacea
  pemphigus vulgaris
  erythema exudativum multiforme
  balanitis
  vulvitis
  hair loss, such as alopecia areata
  cutaneous T-cell lymphoma (vi) Nephropathies, which coincide with inflammatory, allergic and/or proliferative processes:
  Nephrotic syndrome
  all nephritides (vii) Liver diseases which coincide with inflammatory, allergic and/or proliferative processes:
  Acute liver cell decomposition
  acute hepatitis of different origins, e.g., virally-, toxically- or pharmaceutical agent-induced
  chronically aggressive and/or chronically intermittent hepatitis (viii) Gastrointestinal diseases which coincide with inflammatory allergic and/or proliferative processes:
  Regional enteritis (Crohn's disease)
  ulcerative colitis
  gastritis
  reflux esophagitis
  gastroenteritides of other origins, e.g., native sprue (ix) Proctological diseases, which coincide with inflammatory, allergic and/or proliferative processes:
  Anal eczema
  fissures
  hemorrhoids
  idiopathic proctitis (x) Eye disease, which coincide with inflammatory, allergic and/or proliferative processes:
  Allergic keratitis, uveitis, iritis
  conjunctivitis
  blepharitis
  optic neuritis
  chorioiditis
  sympathetic ophthalmia (xi) Diseases of the ear-nose-throat area, which coincide with inflammatory, allergic and/or proliferative processes:
  Allergic rhinitis, hay fever
  otitis externa, e g, caused by contact dermatitis infection, etc.
  otitis media (xii) Neurological diseases which coincide with inflammatory, allergic and/or proliferative proceses:
  Cerebral edema, mainly tumor-induced cerebral edema
  multiple sclerosis
  acute encephalomyelitis
  meningitis
  different forms of convulsions, e.g., infantile nodding spasms (xiii) Blood diseases, which coincide with inflammatory, allergic and/or proliferative processes:
Acquired hemolytic anemia
idiopathic thrombocytopenia
(xiv) Tumor diseases which coincide with inflammatory, allergic and/or proliferative processes:
Acute lymphatic leukemia
malignant lymphoma
lymphogranulomatoses
lymphosarcoma
extensive metastases, mainly in breast, bronchial and prostate cancers
(xv) Endocrine diseases, which coincide with inflammatory, allergic and/or proliferative procsses:
Endocrine orbitopathy
thyrotoxic crisis
de Quervain's thyroiditis
Hashimoto's thyroiditis
hyperthyroidism
(xvi) Organ and tissue transplants, graft-versus-host disease
(xvii) Severe shock conditions, e.g., anaphylactic shock, systemic inflammatory response syndrome (SIRS)
(xviii) Substitution therapy, with
Innate primary suprarenal insufficiency, e.g., congenital adrenogenital syndrome
acquired primary suprarenal insufficiency, e.g., Addison's disease, autoimmune adrenalitis, meta-infective, tumors, metastases, etc.
innate secondary suprarenal insufficiency, e.g., congenital hypopituitarism
acquired secondary suprarenal insufficiency, e.g., meta-infective, tumors, etc.
(xix) Vomiting, which coincides with inflammatory, allergic and/or proliferative processes:
e.g., in combination with a 5-HT$_3$-antagonist in cytostatic-agent-induced vomiting
(xx) Pain with inflammatory origins, e.g., lumbago.

The compounds of general formula I according to the invention can also be used for therapy and prophylaxis of additional pathologic conditions that are not mentioned above, for which synthetic glucocorticoids are now used (see in this connection Hatz, H. J., Glucocorticoide: Immunologische Grundlagen, Pharmakologie und Therapierichtlinien, Wissenschaftliche Verlagsgesellschaft mbH, Stuttgart, 1998).

All previously mentioned indications (i) to (xx) are described in detail in Hatz, H. J., Glucocorticoide: Immunologische Grundlagen, Pharmakologie und Therapierichtlinien, Wissenschaftliche Verlagesgesellschaft mbH, Stuttgart, 1998.

For the therapeutic actions in the above-mentioned pathologic conditions, the suitable dose is different and it depends on, for example, the active strength of the compound of general formula I, the host, the type of administration and the type and severity of the conditions that are to be treated, as well as the use as prophylactic agent or therapeutic agent.

In addition, the invention comprises
(i) The use of a compound of the invention according to formula I or its mixture for the production of a medication for treating a DISEASE;
(ii) a process for treating a DISEASE, and said process comprises an administration of an amount of compound according to the invention, whereby the amount suppresses the disease and whereby the amount of compound is given to a patient who requires such a medication;
(iii) a pharmaceutical composition for treating a DISEASE, and said treatment comprises one of the compounds according to the invention or its mixture and at least one pharmaceutical adjuvant and/or vehicle.

In general, satisfactory results are to be expected in animals when the daily doses comprise a range of 1 μg to 100,000 μg of the compound according to the invention per kg of body weight. In larger mammals, for example humans, a recommended daily dose lies in the range of 1 μg to 100,000 μg per kg of body weight. Preferred is a dose of 10 to 30,000 μg per kg of body weight, more preferably a dose of 10 to 10,000 μg per kg of body weight. For example, this dose is suitably administered several times daily. For treating acute shock (e.g., anaphylactic shock), individual doses can be given that lie considerably above the above-mentioned doses.

The formulation of the pharmaceutical preparations based on the new compounds is carried out in a way that is known in the art, by the active ingredient being processed with the vehicles, fillers, substances that influence decomposition, binding agents, humectants, lubricants, absorbents, diluents, flavoring correctives, staining agents, etc., that are commonly used in galenicals and converted into the desired form of administration. In this case, reference is to be made to Remington's Pharmaceutical Science, 15th Ed. Mack Publishing Company, East Pennsylvania (1980).

For oral administration, especially tablets, coated tablets, capsules, pills, powders, granulates, lozenges, suspensions, emulsions or solutions are suitable.

For parenteral administration, injection and infusion preparations are possible.

For intra-articular injection, correspondingly prepared crystal suspensions can be used.

For intramuscular injection, aqueous and oily injection solutions or suspensions and corresponding depot preparations can be used.

For rectal administration, the new compounds can be used in the form of suppositories, capsules, solutions (e.g., in the form of enemas) and ointments, both for systemic and for local therapy.

For pulmonary administration of the new compounds, the latter can be used in the form of aerosols and inhalants.

For local application to eyes, outer ear channels, middle ears, nasal cavities, and paranasal sinuses, the new compounds can be used as drops, ointments and tinctures in corresponding pharmaceutical preparations.

For topical application, formulations in gels, ointments, fatty ointments, creams, pastes, powders, milk and tinctures are possible. The dosage of the compounds of general formula I should be 0.01%–20% in these preparations to achieve an adequate pharmacological action.

The invention also comprises the compounds of general formula I according to the invention as therapeutic active ingredients. In addition, the compounds of general formula I according to the invention are part of the invention as therapeutic active ingredients together with pharmaceutically compatible and acceptable adjuvants and vehicles. The invention also comprises a pharmaceutical composition that contains one of the pharmaceutically active compounds according to the invention or mixture thereof and a pharmaceutically compatible salt or pharmaceutically compatible adjuvants and vehicles.

Processes for the Production of the Compounds According to the Invention:

The processes that are known from WO98/54159, WO00/32584 and WO02/10143 for the production of compounds according to general formula I can also be used for the production of the compounds of this patent application according to the invention. For synthesis, the nitriles (VII) that are necessary for the production process that is described in WO98/54159, WO00/32584 and WO02/10143 can be obtained by the following process.

Diagram 1:

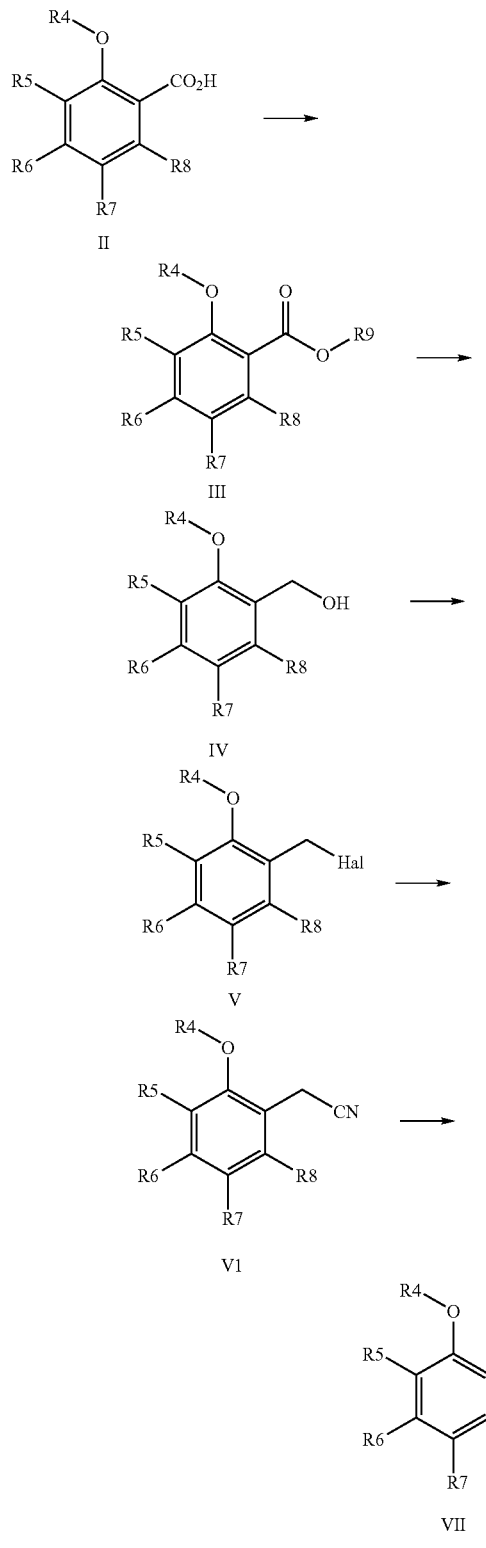

Carboxylic acids of general formula II (radicals R4 to R8 have the meanings that are defined in formula I) are converted according to the methods that are known to one skilled in the art under basic or acidic conditions with a corresponding alkyl halide or with a corresponding alcohol into the corresponding ester with R9. In this case, R9 stands for a C1–C5 alkyl chain. The resulting carboxylic acid esters (III) are reacted with complex hydride reagents, such as, e.g., lithium aluminum hydride, to obtain compounds of formula IV. The alcohols of general formula IV are reacted with an inorganic mixed acid anhydride, such as, e.g., SOCl₂, PCl₃, or PBr₃, to obtain compounds of formula V. The benzyl halides of general formula V are reacted with an inorganic cyanide salt to obtain compounds of formula VI. By reaction of the benzyl cyanides of general formula VI with a strong base, such as, e.g., sodium hydride, potassium carbonate, cesium carbonate or lithium diisopropylamine and a corresponding alkyl halide, compounds of general formula VII are obtained. Radicals R1, R2, R4–R8 of compounds II–VII in Diagram I have the meaning that is indicated in formula I.

In addition, the nitrites of formula VI can be obtained according to the following process.

Diagram 2:

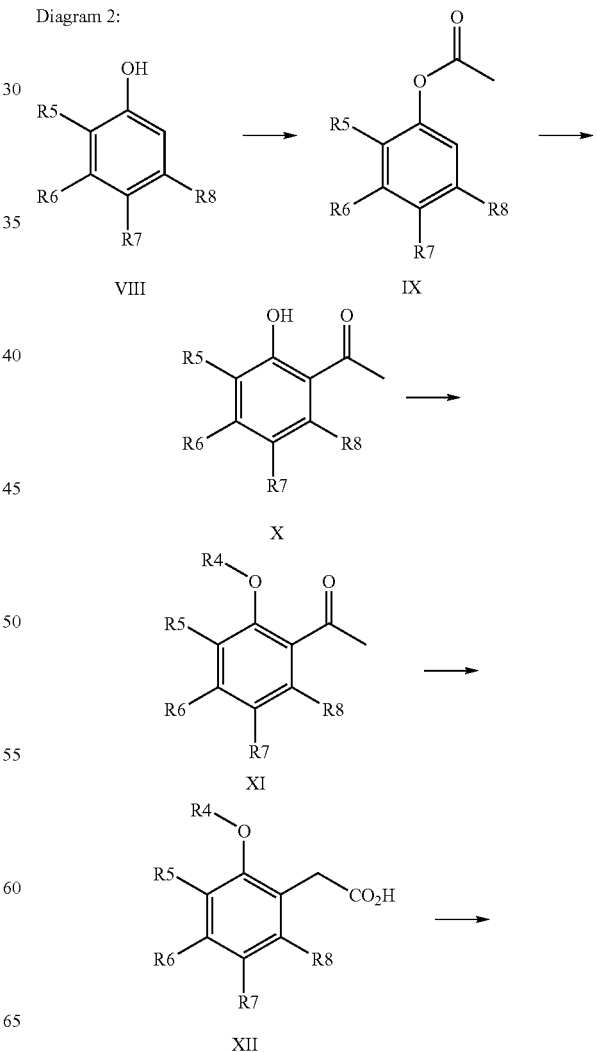

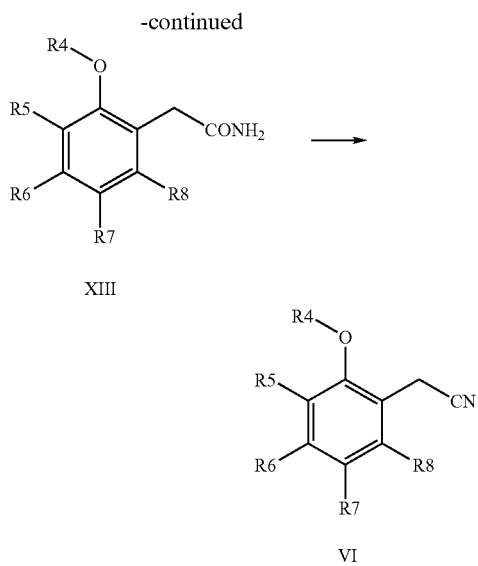

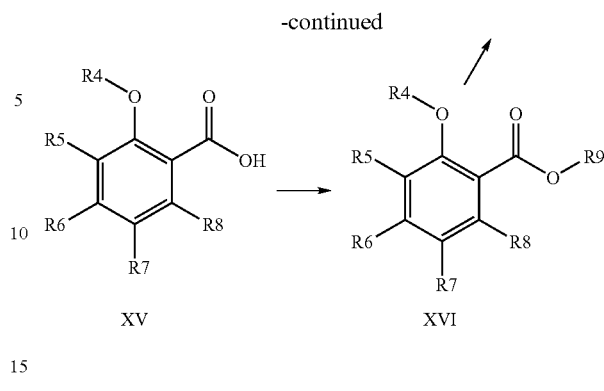

Phenols of general formula VIII are reacted with acetic anhydride to form the corresponding acetates IX, and they are reacted with a Lewis acid, such as, e.g., aluminum trichloride, to form the compounds of general formula X. The compounds of general formula X are reacted with a base, such as, e.g., potassium carbonate, and an alkyl halide to form compounds of general formula XI. The compounds of general formula XI are then reacted according to a process according to Willgerodt and Kindler (Brown, E. V., Synthesis 1975, pp. 358–375) to form phenylacetic acid derivatives of general formula XII. By reaction with an inorganic, mixed acid anhydride, such as, e.g., $SOCl_2$, $PCl_3$ or $PBr_3$ and the subsequent reaction with ammonia, the compounds of general formula XIII are obtained starting from the compounds of formula XII. The compounds of general formula XIII can then be converted by reaction with powerful dehydrating reagents, such as, e.g., $POCl_3$ or $P_2O_5$, into the nitrites of general formula VI. Radicals R4–R8 of the compounds VI–XIII in Diagram 2 have the meaning that is indicated in formula I.

The synthesis of the tertiary alcohols (VIII) that are necessary for the production processes described in WO98/54159, WO00/32584 and/or WO02/10143 can be obtained according to the following processes.

Diagram 3:

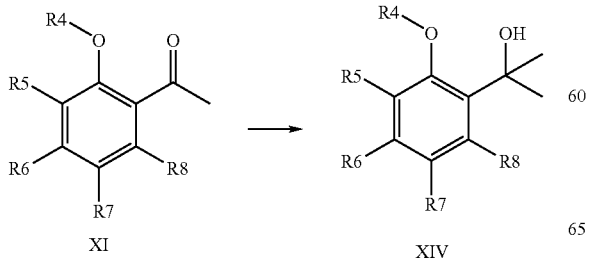

Acetophenone derivatives of general formula XI that are commercially available or that are obtained according to Diagram 2 are reacted with a metal alkyl compound, such as, e.g., methylmagnesium chloride or methylmagnesium bromide, to form the compounds of general formula XIV.

As an alternative, benzoic acid derivatives of general formula XV that can be obtained starting from synthesis methods that are commercially available or that are known according to one skilled in the art can be converted with R9 under basic or acidic conditions with a corresponding alkyl halide or with a corresponding alcohol into the corresponding esters. In this case, R9 stands for a C1–C5 alkyl chain. The resulting carboxylic acid esters XVI are reacted with complex hydride reagents, such as, e.g., lithium aluminum hydride, to obtain compounds of formula XIV.

The creation of the chain and the binding of the methylbenzoxazine part is described in WO98/54159, WO00/32584 and WO02/10143.

The examples below are used for a more detailed explanation of the invention without intending that it be limited to these examples. The syntheses of important precursors and intermediate stages, which are not disclosed within the scope of the experimental part, are already prior art and can be deduced in the example from WO 98/54159, WO00/32584 or WO 02/10143.

Nomenclature:

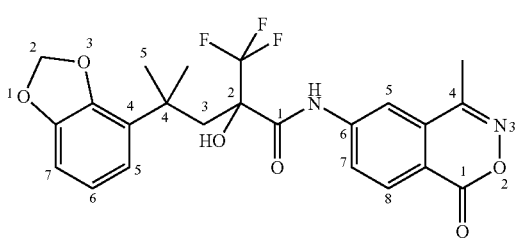

(±)-6-[4-(Benzo[1,3]dioxol-4-yl)-2-hydroxy-4-methyl-2-trifluoromethyl-valeroyl-amino]-4-methyl-2,3-benzoxazin-1-one Experimental Part:

EXAMPLE 1

(±)-6-[4-(Benzo[1,3]dioxol-4-yl)-2-hydroxy-4-methyl-2-trifluoromethyl-valeroyl-amino]-4-methyl-2,3-benzoxazin-1-one

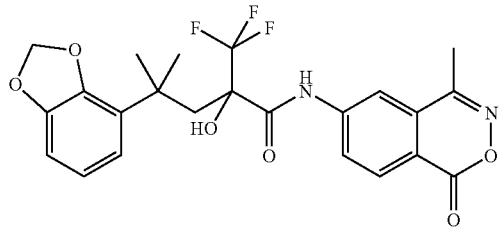

Precursors:

1-(Benz[1,3]dioxol-4-yl)-1-methylethanol 25.5 g of 4-acetylbenzo[1,3]dioxole is mixed with 57.2 ml of methylmagnesium chloride solution (3M in THF) in 375 ml of THF at room temperature under argon. It is stirred for 16 hours at room temperature and added to ice/2H hydrochloric acid. It is extracted with ethyl acetate, and the organic phase is washed with water and brine, and it is dried ($Na_2SO_4$). 27.89 g of 1-[benzo(1,3)dioxol-4-yl]-1-methylethanol is obtained as a brown oil $^1$H-NMR ($CDCl_3$), δ (ppm)=1.6 (s, 6H), 5.95 (s, 2H), 6.76 (dd, 1H), 6.82 (t, 1H), 6.91 (dd, 1H)

4-(Benzo[1,3]dioxol-4-yl)-4-methyl-2-oxo-pentanoic acid 9.5 g of 1-(benzo[1,3]dioxol-4-yl)-1-methylethanol and 14.2 g of 2-trimethylsilyloxy-acrylic acid ethyl ester are mixed in 200 ml of dichloromethane at −70° C. with 47 ml of tin(IV) chloride. After 15 minutes, the solution is added to potassium carbonate solution. After extraction with diethyl ether, the organic phase is washed with water, dried and concentrated by evaporation.

14.4 g of the thus obtained 4-(benzo[1,3]dioxol-4-yl)-4-methyl-2-oxo-pentanoic acid ethyl ester is stirred with 150 ml of 1 M sodium hydroxide and 300 ml of methanol for 10 hours at room temperature. The methanol is then removed in a vacuum, and the remaining solution is extracted with diethyl ether. The aqueous phase is acidified with 1 M hydrochloric acid and extracted with diethyl ether. After drying and concentration by evaporation, 11.1 g of 4-(benzo[1,3]dioxol-4-yl)-4-methyl-2-oxo-pentanoic acid is obtained as a yellowish oil.

MS (ei) m/e: $M^+$=251

6-[4-(Benzo[1,3]dioxol-4-yl)-4-methyl-2-oxo-valeroyl-amino]-4-methyl-2,3-benzoxazin-1-one 10 g of 4-(benzo[1,3]dioxol-4-yl)-4-methyl-2-oxo-pentanoic acid is dissolved in 125 ml of dimethylacetamide and mixed with 3.5 ml of thionyl chloride under argon at −0° C. After 20 minutes of stirring at −3 to +3° C., 7.6 g of 6-amino-4-ethyl-2,3-benzoxazin-1-one (WO00/32584) is added. It is stirred for 96 hours at room temperature, then mixed with water, extracted with ethyl acetate, the organic phase is washed with water, dried ($Na_2SO_4$), and after the solvent is concentrated by evaporation and after chromatography of the crude product on silica gel with hexane/ethyl acetate (100:0→60:40), 6.56 g of 6-[4-(benzo[1,3]dioxol-4-yl)-4-methyl-2-oxo-valeroyl-amino]-4-methyl-2,3-benzoxazin-1-one is obtained as a beige solid.

Flash point=165–166° C., MS (ei) m/e: $M^+$=409

(±)-6-[4-(Benzo[1,3]dioxol-4-yl)-2-hydroxy-4-methyl-2-trifluoromethyl-valeroyl-amino]-4-methyl-2,3-benzoxazin-1-one 2.67 g of 6-[4-(benzo[1,3]dioxol-4-yl)-4-methyl-2-oxo-valeroyl-amino]-4-methyl-2,3-benzoxazin-1-one is dissolved under argon in 35 ml of dimethylformamide and mixed with 4.66 ml of trifluoromethyl-trimethylsilane and 2.6 g of cesium carbonate while being cooled with ice. After 18 hours of stirring at room temperature, a spatula tip full of tetrabutylammonium fluoride is added, and it is stirred for one hour at room temperature. After 300 ml of water is added, it is extracted with ethyl acetate, the organic phase is dried ($Na_2SO_4$) and concentrated by evaporation. The crude product is chromatographed on silica gel. With hexane/ethyl acetate (80:20), 1.33 g of the title compound is obtained in a pure state.

Flash point: 215–218° C.

EXAMPLE 2

(+)-6-[4-(Benzo[1,3]dioxol-4-yl)-2-hydroxy-4-methyl-2-trifluoromethyl-valeroyl-amino]-4-methyl-2,3-benzoxazin-1-one Separation of (±)-6-[4-(benzo[1,3]dioxol-4-yl)-2-hydroxy-4-methyl-2-trifluoromethyl-valeroyl-amino]-4-methyl-2,3-benzoxazin-1-one:

The enantiomer mixture is separated by chromatography on chiral carrier material (CHIRALPAK AD®, DAICEL Company) with hexane/ethanol (95:5, vvv). The (+)-enantiomer with flash point 218–220° C., $[α]_D$+98.9° (c=0.55, $CHCl_3$), is thus obtained.

EXAMPLE 3

(±)-6-[3-(Benzo[1,3]dioxol-4-yl)-cyclopropyl-2-hydroxy-2-trifluoromethyl-propionyl-amino]-4-methyl-2,3-benzoxazin-1-one

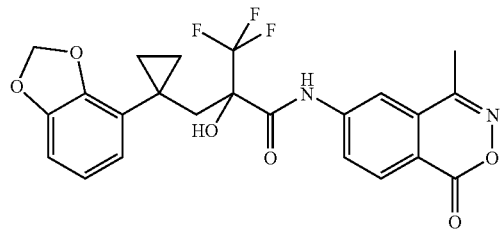

Precursors:

(Benzo[1,3]dioxol-4-yl)-cyclopropyl-carbonitrile 24.8 g of 2,3-methylenedioxybenzaldehyde in 500 ml of methanol and 50 ml of dioxane are mixed in portions at 0° C. with sodium borohydride. After 3 hours of stirring at room temperature, it is concentrated in a vacuum and added to 1N hydrochloric acid/ice water. It is extracted with ethyl acetate, washed with brine, and the organic phase is dried ($Na_2SO_4$) and concentrated by evaporation. 23.6 g of (benzo[1,3]dioxol-4-yl)-methanol, which is mixed in 25 ml of dichloromethane at 0° C. with 26.3 ml of thionyl chloride, is obtained. It is stirred for 2 hours and added to ice water.

It is extracted with ethyl acetate, washed with brine, and the organic phase is dried ($Na_2SO_4$) and concentrated by evaporation.

24.3 g of 2,3-methylenedioxybenzyl chloride is obtained as a red oil. 20 g thereof in 150 ml of ethanol and 45 ml of water is mixed with 14.3 g of sodium cyanide and stirred at 90° C. for 2 hours. It is diluted with water, extracted with ethyl acetate, washed with 2N hydrochloric acid and brine, dried ($Na_2SO_4$) and concentrated by evaporation. 18.68 g of (benzo[2,3]dioxol-4-yl)-acetonitrile is obtained as a brown oil. 9.7 g thereof and 5.3 ml of 1,2-dibromomethane in 100 ml of dimethylformamide are mixed at 0° C. with 4.9 g of sodium hydride (60% in oil) and stirred for 12 hours at room temperature. It is added to water, extracted with ether, and the organic phase is washed 5 times with water, dried ($Na_2SO_4$) and concentrated by evaporation. 8.24 g of the title compound is obtained.

$^1$H-NMR (CDCl$_3$), δ (ppm)=1.50–1.58 (m, 2H), 1.59–1.67 (m, 2H), 6.0 (s, 2H), 6.75–6.92 (m, 3H)

3-(Benzo[2,3]dioxol-4-yl)cyclopropyl-acrylic acid ethyl ester

A solution of 8.2 g of (benzo[1,3]dioxol-4-yl)-cyclopropyl-carbonitrile in 66 ml of toluene is mixed at −70° C. with 45 ml of a 1.2 M diisobutylaluminum hydride-toluene solution. After 4 hours at −70° C., it is mixed with 33 ml of ethyl acetate and stirred overnight at room temperature. The batch is added to ethyl acetate/water and filtered through diatomaceous earth. The organic phase is separated and washed with brine, dried ($Na_2SO_4$) and concentrated by evaporation. 6.1 g of (benzo[1,3]dioxol-4-yl)-cyclopropyl-carbaldehyde is obtained. The latter is added to a solution, prepared at −78° C. and tempered to 0° C., of 8.92 g of phosphonoacetic acid triethyl ester and 17.3 ml of lithium diisopropylamine (2 M in heptane/ethylbenzene/THF) in 45 ml of THF, and it is stirred for 12 hours at room temperature. The batch is mixed with saturated $NH_4Cl$ and diluted with ethyl acetate and water. The phases are separated, the aqueous phase is extracted with ethyl acetate, and the combined organic extracts are washed with brine, dried ($Na_2SO_4$) and concentrated by evaporation. 9.3 g of 3-(benzo[2,3]dioxol-4-yl)cyclopropyl-acrylic acid ethyl ester is obtained as a beige solid.

$^1$H-NMR (CDCl$_3$), δ (ppm)=1.26 (t, 3H), 1.19–1.39 (m, 4H), 4.15 (q, 2H), 5.4 (d, 1H), 5.96 (s, 2H), 6.6 (d, 1H), 6.7–6.85 (m, 3H)

3-(Benzo[1,3]dioxol-4-yl)-cyclopropyl-2-hydroxypropionic acid ethyl ester 9.2 g of -(benzo[2,3]dioxol-4-yl)cyclopropyl-acrylic acid ethyl ester is stirred in 150 ml of ethanol in the presence of 0.9 g of 10% palladium/activated carbon catalyst for 15 hours in a hydrogen atmosphere (1 atm). The batch is filtered on Celite and concentrated by evaporation. 7.1 g of-(benzo [2,3]dioxol-4-yl)cyclopropyl-propionic acid ethyl ester is obtained. 5.9 g thereof is dissolved in 78 ml of THF and treated at −78° C. with 62.9 ml of potassium hexamethyldisilazide-toluene solution (0.5 M). After 30 minutes, 8.2 g of 3-phenyl-2-phenylsulfonyloxaziridine (F. A. Davis, S. Chattopadhyay, J. C. Towson, S. Lal, T. Reddy *J. Org. Chem.* 1988, 53, 2087) in 78 ml of THF is added in drops thereto and stirred for 1 hour at −78° C. The batch is mixed with saturated $NH_4Cl$ and heated within 1 hour to room temperature. THF is removed in a vacuum, the residue is taken up in ether, the solid is filtered off, the phases are separated, and the aqueous phase is extracted with ether. The combined organic extracts are washed with brine, dried ($Na_2SO_4$) and concentrated by evaporation. Column chromatography on silica gel with hexane/ethyl acetate (100: 0→80:20) yields 4.85 g of 3-(benzo[1,3]dioxol-4-yl)-cyclopropyl-2-hydroxypropionic acid ethyl ester.

$^1$H-NMR (CDCl$_3$), δ (ppm)=0.79–0.91 (m, 4H), 1.23 (t, 3H), 1.82 (dd, 1H), 2.21 (dd, 1H), 3.97–4.18 (m, 3H), 5.99 (s, 2H), 6.70 (dd, 1H), 6.76 (t, 1H), 6.82 (dd, 1H).

3-(Benzo[1,3]dioxol-4-yl)-cyclopropyl-2-oxopropionic acid 13.9 g of 1,1,1-triacetoxy-1,1-dihydro-1,2-benzodioxol-3 (1H)-one (Dess-Martin-Periodinane, cf. D. B. Dess, J. C. Martin, *J. Am. Chem. Soc.* 1991, 113, 7277) is added to a solution of 4.55 g of 3-(benzo[1,3]dioxol-4-yl)-cyclopropyl-2-hydroxypropionic acid ethyl ester in 205 ml of dichlormethane. After 6 hours at room temperature, the batch is added to a saturated solution of sodium thiosulfate and extracted with ether. It is washed with water, saturated bicarbonate solution and brine, dried ($Na_2SO_4$) and concentrated by evaporation. The residue is purified by column chromatography on silica gel with hexane-ethyl acetate (100: 0→80:20). 2.52 g of 3-(benzo[1,3]dioxol-4-yl)-cyclopropyl-2-oxopropionic acid ethyl ester is obtained. The latter is stirred in 84 ml of a solution of 1N sodium hydroxide solution in ethanol/water 2:1 at room temperature for 12 hours. The batch is concentrated in a vacuum, and the remaining solution is extracted with diethyl ether. The aqueous phase is acidified with 1 M hydrochloric acid and extracted with diethyl ether. After drying and concentration by evaporation, 2.2 g of 3-(benzo[1,3]dioxol-4-yl)-cyclopropyl-2-oxopropionic acid is obtained as a yellowish oil.

$^1$H-NMR (CDCl$_3$), δ (ppm)=0.9–0.95 (m, 2H), 0.98–1.06 (m, 2H), 3.21 (s, 2H), 5.92 (s, 2H), 6.63–6.79 (m, 3H).

6-[3-(Benzo[1,3]dioxol-4-y)-cyclopropyl-2-oxopropionyl-amino]-4-methyl-2,3-benzoxazin-1-one 855 mg of the title compound is obtained as a colorless solid from 2.2 g of 3-(benzo[1,3]dioxol-4-yl)-cyclopropyl-2-oxopropionic acid and 1.78 g of 6-amino-4-ethyl-2,3-benzoxazin-1-one analogously to the described process for 6-[4-(benzo[1,3]dioxol-4-yl)-4-methyl-2-oxo-valeroyl-amino]-4-methyl-2,3-benzoxazin-1-one.

Fp.: 185–186° C., MS (ei) m/e: M$^+$=406.

(±)-6-[3-(Benzo[1,3]dioxol-4-yl)-cyclopropyl-2-hydroxy-2-trifluoromethyl-propionyl-amino]-4-methyl-2,3-benzoxazin-1-one 170 mg of the title compound is obtained as a colorless solid from 840 mg of 6-[3-(benzo[1,3]dioxol-4-yl)-cyclopropyl-2-oxopropionyl-amino]-4-methyl-2,3-benzoxazin-1-one analogously to the described process for 6-[4-(benzo[1,3]dioxol-4-yl)-2-hydroxy-4-methyl-2-trifluoromethyl-valeroyl-amino]-4-methyl-2,3-benzoxazin-1-one.

MS (ei) m/e: M$^+$=477.

EXAMPLE 4

(+)-6-[3-(Benzo [1,3]dioxol-4-yl)-cyclopropyl-2-hydroxy-2-trifluoromethyl-propionyl-amino]-4-methyl-2,3-benzoxazin-1-one Separation of (±)-6-[3-(benzo[1,3]dioxol-4-yl)-cyclopropyl-2-hydroxy-2-trifluoromethyl-propionyl-amino]-4-methyl-2, 3-benzoxazin-1-one:

The enantiomer mixture is separated by chromatography on chiral carrier material (CHIRALPAK AD®, DAICEL Company) with hexane/ethanol (95:5, vvv). The (+)-enantiomer with flash point 218–219° C., [α]$_D$+82° (c=0.70, CHCl$_3$), is thus obtained.

EXAMPLE 5

(±)-6-[3-(Benzo[1,3]dioxol-4-yl)-cyclobutyl-2-hydroxy-2-trifluoromethyl-propionyl-amino]-4-methyl-2,3-benzoxazin-1-on

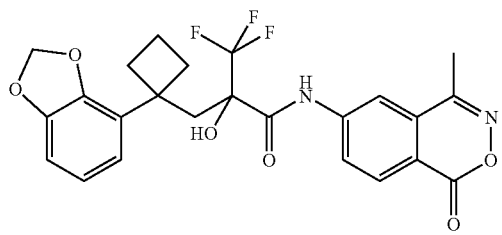

Precursors:

(Benzo[1,3]dioxol-4-yl)-cyclobutyl-carbonitrile

Analogously to the described process for (benzo[1,3]dioxol-4-yl)-cyclopropyl-carbonitrile, and starting from 10 g of (benzo[2,3]dioxol-4-yl)-acetonitrile and 8.2 ml of 1,3-dibromopropane, 4.8 g of (benzo[1,3]dioxol-4-yl)-cyclobutyl-carbonitrile is obtained as a pale yellow oil.

$^1$H-NMR (CDCl$_3$), δ (ppm)=2.0–2.21 (m, 1H), 2.36–2.52 (m, 1H), 2.76 (d, 2H), 2.78 (d, 2H), 6.01 (s, 2H), 6.75–6.89 (m, 3H).

3-(Benzo[1,3]dioxol-4-yl)-cyclobutyl-2-oxopropionic acid 4.8 g of (benzo[1,3]dioxol-4-yl)-cyclobutyl-carbonitrile, dissolved in 45 ml of toluene, is slowly mixed at −70° C. with 20.2 ml of 1,2 M diisobutylaluminium hydride solution in toluene. After 4 hours at −78° C., 15 ml of ethyl acetate is added in drops. It is heated to room temperature, added to water/ethyl acetate and filtered through diatomaceous earth. The water phase is extracted with ethyl acetate, and the combined organic phases are dried (Na$_2$SO$_4$) and concentrated by evaporation. After chromatography on silica gel with hexane-ethyl acetate (80:20), 3.05 g of (benzo[1,3]dioxol-4-yl)-cyclobutyl-carbaldehyde is obtained. The latter is added to a solution, prepared at −78° C. and tempered to 0° C., of 3.9 g of 2-diethylphosphono-2-ethoxyacetic acid ethyl ester and 7.9 ml of lithium diisopropylamine (2 M in heptane/ethylbenzene/THF) in 25 ml of water, and it is stirred for 12 hours at room temperature. The reaction mixture is added to water, extracted with ethyl acetate, washed with brine, dried (Na$_2$SO$_4$) and concentrated by evaporation. The crude product is stirred in 137 ml of a solution of 1N sodium hydroxide solution in ethanol/water 2:1 at room temperature for 12 hours. The batch is concentrated in a vacuum, and the remaining solution is extracted with diethyl ether. The aqueous phase is acidified with 1 M hydrochloric acid and extracted with diethyl ether. 2.95 g of acid, which is refluxed for several hours with 55 ml of 2N sulfuric acid and 10 ml of glacial acetic acid while being stirred vigorously, is obtained. After extraction with ethyl acetate and washing with water, 1.66 g of 3-(benzo[1,3]dioxol-4-yl)-cyclobutyl-2-oxopropionic acid is obtained as a yellowish oil.

$^1$H-NMR (CDCl$_3$), δ (ppm)=1.82–1.99 (m, 2H), 2.22–2.35 (m, 2H), 2.46–2.59 (m, 2H), 3.54 (s, 2H), 5.9 (s, 2H), 6.68–6.74 (m, 2H), 6.79 (t, 1H).

6-[3-(Benzo[1,3]dioxol-4-yl)-cyclobutyl-2-oxopropionyl-amino]-4-methyl-2,3-benzoxazin-1-one mg of the title compound is obtained as a colorless solid from 1.6 g of 3-(benzo[1,3]dioxol-4-yl)-cyclobutyl-2-oxopropionic acid and 1.2 g of 6-amino-4-ethyl-2,3-benzoxazin-1-one analogously to the described process for 6-[4-(Benzo[1,3]dioxol-4-yl)-4-methyl-2-oxo-valeroyl-amino]-4-methyl-2,3-benzoxazin-1-one.

Flash point: 180–183° C., $^1$H-NMR (CDCl$_3$), δ (ppm) =1.88–2.01 (m, 1H), 2.08–2.21 (m, 1H), 2.27–2.39 (m, 2H), 2.5–2.62 (m, 2H), 2.58 (s, 3H), 3.67 (s, 2H), 5.92 (s, 2H), 6.63–6.69 (m, 1H), 6.7–6.76 (m, 2H), 7.71 (dd, 1H), 8.16 (d, 1H), 8.34 (d, 1H, 8.92 (s, 1H).

(±)-6-[3-(Benzo[1,3]dioxol-4-yl)-cyclobutyl-2-hydroxy-2-trifluoromethyl-propionyl-amino]-4-methyl-2,3-benzoxazin-1-one 402 mg of the title compound is obtained as a colorless solid from 550 mg of 6-[3-(benzo[1,3]dioxol-4-yl)-cyclobutyl-2-oxopropionyl-amino]-4-methyl-2,3-benzoxazin-1-one analogously to the described process for 6-[4-(benzo[1,3]dioxol-4-yl)-2-hydroxy-4-methyl-2-trifluoromethyl-valeroyl-amino]-4-methyl-2,3-benzoxazin-1-one.

Flash point: 170–171° C., MS (ei) m/e: M$^+$=492.

EXAMPLE 6

(+)-6-[3-(Benzo[1,3]dioxol-4-yl)-cyclobutyl-2-hydroxy-2-trifluoromethyl-propionyl-amino]-4-methyl-2,3-benzoxazin-1-one Separation of (±)-6-[3-(benzo[1,3]dioxol-4-yl)-cyclobutyl-2-hydroxy-2-trifluoromethyl-propionyl-amino]-4-methyl-2,3-benzoxazin-1-one The enantiomer mixture is separated by chromatography on chiral carrier material (CHIRALPAK AD®, DAICEL Company) with hexane/ethanol (93:7, vvv). The (+)-enantiomer with flash point 115–117° C., [α]$_D$+74.3° (c=0.7, CHCl$_3$), is thus obtained.

EXAMPLE 7

(+)-6-[4-(5-Bromo-2-hydroxyphenyl)-2-hydroxy-4-methyl-2-(trifluoromethyl)valeroylamino]-4-methyl-2,3-benzoxazin-1-one

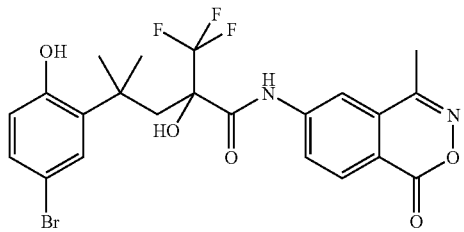

Precursors:

(±)-6-[4-(5-Bromo-2-methoxyphenyl)-2-hydroxy-4-methyl-2-(trifluoromethyl)valeroylamino]-4-methyl-2,3-benzoxazin-1-one (±)-6-[4-(5-Bromo-2-methoxyphenyl)-2-hydroxy-4-methyl-2-(trifluoromethyl)valeroylamino]-4-methyl-2,3-benzoxazin-1-one is produced according to analogous instructions from Example 1. Flash point 175–176° C.

(+)-6-[4-(5-Bromo-2-methoxyphenyl)-2-hydroxy-4-methyl-2-(trifluoromethyl)valeroylamino]-4-methyl-2,3-benzoxazin-1-one Separation of (±)-6-[4-(5-Bromo-2-methoxyphenyl)-2-hydroxy-4-methyl-2-(trifluoromethyl)valeroyl-amino]-4-methyl-2,3-benzoxazin-1-one:

The enantiomer mixture is separated by chromatography on chiral carrier material (CHIRALPAK AD®, DAICEL Company) with hexane/ethanol (95:5, vvv). The (+)-enantiomer with flash point 198–199° C., $[\alpha]_D$+119.0° (c=0.17, THF), is thus obtained.

EXAMPLE 7

(+)-6-[4-(5-Bromo-2-hydroxyphenyl)-2-hydroxy-4-methyl-2-(trifluoromethyl)valeroylamino]-4-methyl-2,3-benzoxazin-1-one 43.2 mg of (+)-6-[4-(5-bromo-2-methoxyphenyl)-2-hydroxy-4-methyl-2-(trifluoromethyl)valeroylamino]-4-methyl-2,3-benzoxazin-1-one in 2.5 ml of dichloromethane and 0.4 ml of 1 M boron tribromide in dichloromethane are stirred for 1.5 hours at 0° C. and mixed with ethyl acetate and sodium bicarbonate solution. The organic phase is washed with water, dried, concentrated by evaporation, and the residue is chromatographed on silica gel (hexane/ethyl acetate, 1.5+1). After crystallization from diisopropyl ether, 34 mg of (+)-6-[4-(5-bromo-2-hydroxyphenyl)-2-hydroxy-4-methyl-2-(trifluoromethyl)valeroylamino]-4-methyl-2,3-benzoxazin-1-one is obtained.

MS, flash point 237–239, $[\alpha]_D$+99.6°, (c=0.5, chloroform)

EXAMPLE 8

(+)-4-Ethyl-6-[4-(7-benzofuranyl)-2-hydroxy-4-methyl-2-trifluoromethylvaleroylamino]-2,3-benzoxazin-1-one

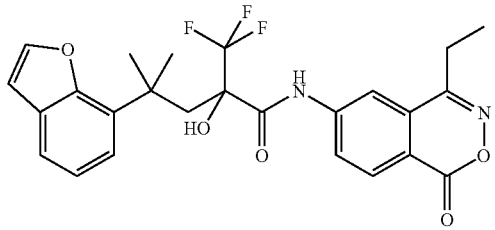

Precursors:

(±)-4-Ethyl-6-[4-(2,3-dihydrobenzofuran-7-yl)-2-hydroxy-4-methyl-2-(trifluoromethyl)valeroylamino]-2,3-benzoxazin-1-one (±)-4-Ethyl-6-[4-(2,3-dihydrobenzofuran-7-yl)-2-hydroxy-4-methyl-2-(trifluoromethyl)valeroylamino]-2,3-benzoxazin-1-one is produced according to analogous instructions from Example 1, flash point 198° C.

(±)-4-Ethyl-6-[4-(7-benzofuranyl)-2-hydroxy-4-methyl-2-trifluoromethylvaleroylamino]-2,3-benzoxazin-1-one 930 mg of (±)-4-ethyl-6-[4-(2,3-dihydrobenzofuran-7-yl)-2-hydroxy-4-methyl-2-trifluoromethylvaleroylamino]-2,3-benzoxazin-1-one and 680 mg of 2,3-dichloro-5,6-dicyano-p-benzoquinone in 90 ml of dioxane are refluxed for 20 hours, mixed with water and suctioned off. After chromatography on silica gel (hexane/ethyl acetate 1.5+1), 810 mg of (±)-4-ethyl-6-[4-(7-benzofuranyl)-2-hydroxy-4-methyl-2-(trifluoromethyl)valeroylamino]-2,3-benzoxazin-1-one is obtained. Flash point 212° C.

EXAMPLE 8

(±)-4-Ethyl-6-[4-(7-benzofuranyl)-2-hydroxy-4-methyl-2-(trifluoromethyl)valeroylamino]-2,3-benzoxazin-1-one Separation of (±)-4-ethyl-6-[4-(7-benzofuranyl)-2-hydroxy-4-methyl-2-trifluoromethylvaleroylamino]-2,3-benzoxazin-1-one:

The enantiomer mixture is separated by chromatography on chiral carrier material (CHIRALPAK AD®, DAICEL Company) with hexane/ethanol (95:5, vvv). The (+)-enantiomer with flash point 219° C., $[\alpha]_D$+25.1° (c=0.5, CHCl$_3$), is thus obtained.

EXAMPLE 9

(+)-6-[4-(5-Fluorobenzoxazol-7-yl)-2-hydroxy-4-methyl-2-trifuoromethylvaleroylamino]-methyl-42,3-benzoxazin-1-one

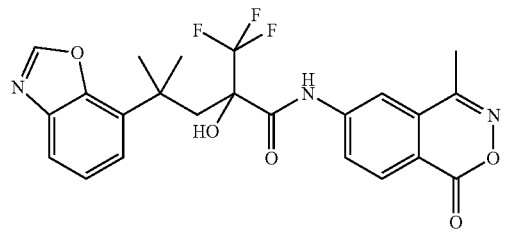

Precursors:

(−)-6-[4-(5-Fluoro-2-hydroxy-3-nitrophenyl)-2-hydroxy-4-methyl-2-(trifluoromethyl)valeroyl-amino]-4-methyl-2,3-benzoxazin-1-one 1.6 g of (±)-6-[4-(5-fluoro-2-hydroxyphenyl)-2-hydroxy-4-methyl-2-(trifluoromethyl)valeroylamino]-4-methyl-2,3-benzoxazin-1-one in 90 ml of ethyl acetate and 40 ml of trifluoroacetic acid are mixed at −10° C. with 3.5 ml of nitric acid, stirred for 0.5 hour at −10° C. and for 5 hours at 0° C., added to sodium bicarbonate solution and extracted with dichloromethane. The dichloromethane phase is dried and concentrated by evaporation. The residue is purified on a silica gel column (hexane/ethyl acetate 1.5+1). After crystallization from diisopropyl ether, 570 mg of (±)-6-[4-(5-fluoro-2-hydroxy-3-nitrophenyl)-2-hydroxy-4-methyl-2-(trifluoromethyl)valeroylamino]-4-methyl-2,3-benzoxazin-1-one is. Flash point 198–199° C.

Separation of enantiomers:

(−)-6-[4-(5-Fluoro-2-hydroxy-3-nitrophenyl)-2-hydroxy-4-methyl-2-(trifluoromethyl)valeroyl-amino]-4-methyl-2,3-benzoxazin-1-one The enantiomer mixture is separated by chromatography on chiral carrier material (CHIRALPAK AD®, DAICEL Company) with hexane/ethanol (85:15, vvv). The (−)-enantiomer with $[\alpha]_D$−37.8° (c=0.5, THF) is thus obtained.

(+)-6-[4-(5-Fluorobenzoxazol-7-yl)-2-hydroxy-4-methyl-2-(trifluoromethyl)valeroylamino]-4-methyl-2,3-benzoxazin-1-one.

103 mg of (−)-6-[4-(5-fluoro-2-hydroxy-3-nitrophenyl)-2-hydroxy-4-methyl-2-(trifluoromethyl)valeroyl-amino]-4-methyl-2,3-benzoxazin-1-one in 5 ml of tetrahydrofuran and 1 ml of acetic acid are stirred for 2.5 hours with 300 mg of iron, mixed with 0.5 ml of orthoformic acid triethyl ester and ethyl acetate, suctioned off and concentrated by evaporation after standing for 4 hours at room temperature. The residue is dissolved in ethyl acetate and mixed with 0.05 ml of orthoformic acid. After 20 hours at room temperature, 72 mg of (+)-6-[4-(5-fluorobenzoxazol-7-yl)-2-hydroxy-4-methyl-2-(trifluoromethyl)valeroylamino]-4-methyl-2,3-benzoxazin-1-one is suctioned off. MS, flash point 276–277° C., (+)-enantiomer with $[\alpha]_D$+53.0° (c=0.25, THF).

EXAMPLE 10

(+)-6-[3-(2-Methoxy-3-fluoro-phenyl)-cyclopropyl-2-hydroxy-2-trifluoromethyl-propionylamino]-4-methyl-2,3-benzoxazin-1-one

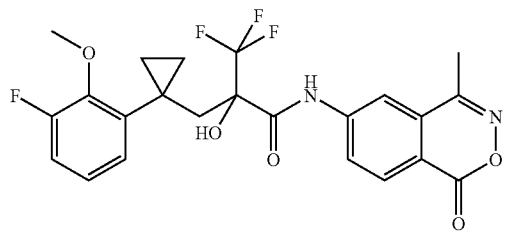

Precursors:

(2-Methoxy-3-fluoro-phenyl)-cyclopropyl-carbonitrile 5 g (34.7 mmol) of 2,6-difluoroanisole and 2.62 g (40 mmol) of cyclopropylnitrile are added in 100 ml of toluene. At room temperature, 77 ml of a 0.5 M solution of KHMDS in toluene is added in drops. The reaction mixture is heated slightly. After stirring overnight at room temperature, water and ethyl acetate are added. It is shaken with 10% sulfuric acid, and the organic phase is separated. After repeated shaking of the aqueous phase with ethyl acetate, the combined organic extracts are washed with brine. After drying on sodium sulfate, it is filtered off, and the solvent is spun off. After chromatography on silica gel (mobile solvent: ethyl acetate/hexane), 2.53 g (38.2%) of the desired compound is obtained.

MS (CI) m/e (relative intensity): 209 ($M^+$+18, 100).

(+)-6-[4-(2-Methoxy-3-fluoro-phenyl)-cyclopropyl-2-hydroxy-2-trifluoromethyl-propanoylamino]-4-methyl-2,3-benzoxazin-1-one (+)-6-[4-(2-Methoxy-3-fluoro-phenyl)-cyclopropyl-2-hydroxy-2-trifluoromethyl-propanoylamino]-4-methyl-2,3-benzoxazin-1-one is obtained starting from (2-methoxy-3-fluoro-phenyl)-cyclopropyl-carbonitrile according to the process that is described in Example 3.

MS (FAB) m/e (relative intensity): 481 ($M^+$+1, 45)

Produced according to the processes described above were the following substances of Table 2:

TABLE 2

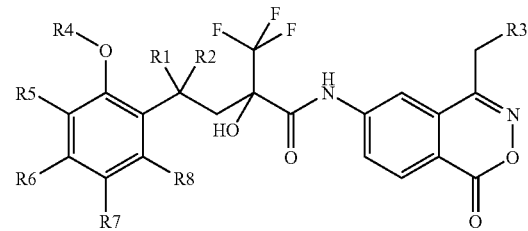

| Ex. | Analogous Ex. | R1/R2 | R4–R8 (≠H) | R3 | MS* | Fp [° C.] | Isomerism** |
|---|---|---|---|---|---|---|---|
| 11 | 1 | $CH_3$, $CH_3$ | R4–R5 = —$CH_2$—O— | $CH_3$ | (ei) 492 ($M^+$) | 248–250 | +61 ($CHCl_3$) |
| 12 | 3 | —$(CH_2)_2$— | R4–R5 = —$CH_2$—$CH_2$— | H | (ei) 474 ($M^+$) | 249–255 | Racemate |
| 13 | 3 | —$(CH_2)_2$— | R4–R5 = —$CH_2$—$CH_2$— | H | (ei) 474 ($M^+$) | 249–255 | +140 ($CHCl_3$) |
| 14 | 3 | —$(CH_2)_3$— | R4–R5 = —$CH_2$—$CH_2$— | H | (ei) 489 ($M^+$) | 205–213 | Racemate |
| 15 | 3 | —$(CH_2)_3$— | R4–R5 = —$CH_2$—$CH_2$— | H | (ei) 489 ($M^+$) | 205–213 | +46.7 ($CHCl_3$) |
| 16 | 3 | —$(CH_2)_3$— | R4–R5 = —$CH_2$—$CH_2$— | $CH_3$ | (ei) 503 ($M^+$) | 195–199 | Racemate |
| 17 | 3 | —$(CH_2)_3$— | R4–R5 = —$CH_2$—$CH_2$— | $CH_3$ | (ei) 503 ($M^+$) | 195–199 | +101.9 ($CHCl_3$) |
| 18 | 1 | $CH_3$, $CH_3$ | R7 = F, R4–R5 = —$CH_2$—O— | H | | 215–217 | Racemate |
| 19 | 1 | $CH_3$, $CH_3$ | R7 = F, R4–R5 = —$CH_2$—O— | H | | 215–217 | +53.3 ($CHCl_3$) |
| 20 | 1 | $CH_3$, $CH_3$ | R6 = Br, R4–R5 = —$CH_2$—O— | H | (ei) 557 ($M^+$) | 259–261 | +36.8 ($CHCl_3$) |

TABLE 2-continued

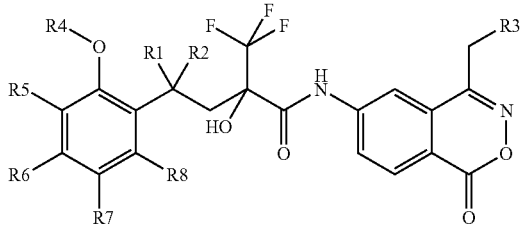

| Ex. | Analogous Ex. | R1/R2 | R4–R8 (≠H) | R3 | MS* | Fp [° C.] | Isomerism** |
|---|---|---|---|---|---|---|---|
| 21 | 3 | —$(CH_2)_2$— | R4 = $CH_3$, R6 = I | H | (ei) 587 ($M^+$) | 208–209 | +68.6 ($CHCl_3$) |
| 22 | 4 | $CH_3$, $CH_3$ | R5 = R7 = F | H |  | 108–112 | +127.8 ($CHCl_3$) |
| 23 | 5 | $CH_3$, $CH_3$ | R4–R5 = —CH=CH— | H | (ei) 475 ($M^+$) | 235–236 | +88.3 ($CHCl_3$) |
| 24 | 5 | $(CH_2)_3$ | R4–R5 = —CH=CH— | H | (ei) 502 ($M^+$) |  | +3.5 ($CHCl_3$) |
| 25 | 4 | —$(CH_2)_2$— |  | H | (ei) 449 ($M^+$) | 293–296 | +7.7 ($CHCl_3$) |
| 26 | 6 | —$(CH_2)_3$— | R4–R5 = —CH=N—, R6 = F | H |  | 276–277 | Racemate |
| 27 | 6 | —$(CH_2)_3$— | R4–R5 = —CH=N—, R6 = F | H |  | 276–277 | +84.0 (THF) |
| 28 | 4 | —$(CH_2)_3$— | R7 = F | H |  | 138 | Racemate |
| 29 | 4 | —$(CH_2)_3$— | R7 = F | H |  | 138 | +60.4 (THF) |
| 30 | 7 | —$(CH_2)_2$— | R5 = F | H | (esi) 467 ($M^+$ + 1) |  | +97.5 (THF) |
| 31 | 7 | —$(CH_2)_3$— | R4 = $CH_3$, R5 = F | H | (FAB) 495 ($M^+$ + 1) |  | Racemate |
| 32 | 7 | —$(CH_2)_3$— | R4 = $CH_3$, R5 = F | H | (FAB) 495 ($M^+$ + 1) |  | (+) |
| 33 | 4 | —$(CH_2)_3$— | R5 = F | H | (esi) 481 ($M^+$ + 1) |  | +78.7 (THF) |
| 34 | 7 | $CH_3$, $CH_3$ | R5 = F | H | (esi) 469 ($M^+$ + 1) |  | +70.2 (THF) |
| 35 | 7 | $CH_3$, $CH_2CH_3$ | R5 = F | H | (esi) 483 ($M^+$ + 1, 50) |  | +96.4 (THF) |

*(Method): MS is mass spectroscopy, (EI = electron impact, esi = electron spray ionization, FAB = fast atom bombardment, m/e (relative intensity)
**(Method): specific angle of rotation at 20° C.; if no specific angle of rotation is indicated, the direction of rotation was measured by polarimetric detection in HPLC

EXAMPLE 11

In the glucocorticoid receptor-(GR) binding test with use of cytosol preparations of Sf9 cells, which have expressed the human GR, and of 10 nmol of [$^3$H]-dexamethasone as a reference substance (cf. Lefebvre et al., 33, 557–563, 1989), the compounds of formula I show a high to very high affinity to the GR ($IC_{50}$<4 nM) (see Table 3), whereby the binding affinity of the racemic compounds is lower than that of the pure enantiomer.

TABLE 3

| GR-Binding Data | |
|---|---|
| Compound | $IC_{50}$ [mol/l]$^{-9}$ |
| Example 1 | 1.5 × $10^{-9}$ |
| Example 2 | <3.0 × $10^{-10}$ |
| Example 12 | 8.5 × $10^{-10}$ |
| Example 13 | <3.0 × $10^{-10}$ |
| Example 16 | 1.3 × $10^{-8}$ |
| Example 17 | 4.5 × $10^{-9}$ |
| Example 28 | 2.0 × $10^{-9}$ |
| Example 29 | 3.5 × $10^{-10}$ |
| Example 31 | 1.4 × $10^{-8}$ |
| Example 32 | 3.0 × $10^{-9}$ |

TABLE 3-continued

| GR-Binding Data | |
|---|---|
| Compound | $IC_{50}$ [mol/l]$^{-9}$ |
| Dexamethasone | 2.8 × $10^{-8}$ |
| Prednisolone | 4.0 × $10^{-8}$ |

EXAMPLE 12

The potency of the inflammation inhibition is determined by the inhibition of the secretion of cytokine IL-8 in a cellular test. The compounds of general formula I according to the invention inhibit the secretion of IL-8, triggered by lipopolysaccharide (LPS), in human monocyte cell line THP-1. The concentration of the cytokine was determined in the supernatant by commercially available ELISA kits. In this connection, the compounds of formula I show a high to very high potency and action (>50%) in the inhibition (see Table 4). The potency of the racemates is considerably lower than that of the pure enantiomers.

TABLE 4

Inhibition of the IL-8 Secretion

| Compounds | Inhibition of IL-8 Secretion $IC_{50}$ [mol/l] | Inhibition of IL-8 Secretion Efficacy [%] |
|---|---|---|
| Example 1 | $7.6 \times 10^{-8}$ | 51 |
| Example 2 | $2.9 \times 10^{-8}$ | 57 |
| Example 3 | $3.9 \times 10^{-8}$ | 53 |
| Example 4 | $2.9 \times 10^{-8}$ | 62 |
| Example 12 | $4.2 \times 10^{-8}$ | 52 |
| Example 13 | $3.7 \times 10^{-8}$ | 68 |
| Example 14 | $7.1 \times 10^{-8}$ | 61 |
| Example 15 | $7.5 \times 10^{-9}$ | 74 |
| Example 28 | $8.6 \times 10^{-7}$ | 100 |
| Example 29 | $3.1 \times 10^{-8}$ | 86 |
| Prednisolone | $1.8 \times 10^{-8}$ | 92 |

EXAMPLE 13

The compounds of formula I are preferably able to induce the transrepression by the GR and, to a weaker extent, the transactivation. This dissociation of the mechanisms of action was determined with the aid of the reporter gene test in stable transfixed human HeLa cells. To determine the transactivation induced by the GR, the MMTV promoter, which is set before a luciferase gene, is used. Via the photometric determination of the luciferase activity, it was possible to determine the transactivation activities of the GR after binding the test compounds. The inhibition of the transcription of the luciferase gene, induced by tetradecanoyl-phorbol acetate (TPA) under the control of the IL-6 promoter or the collagenase promoter (transpression) by the GR after binding the test substances, was also determined by the measurement of luciferase activity in HeLa cells. The compounds of formula I show a more than 5×-better potency in transrepression (IL-6 promoter) than in the transactivation (MMTV promoter) and an at least 60% inhibition of the IL-6 activity or the collagenase-promoter activity. In the transrepression, the pure enantiomers, compared to the racemic compounds, show a better activity (potency).

TABLE 5

Transrepression Data in the Reporter Gene Test

| Compound | Transrepression (TR)(IL-6-Promoter) $IC_{50}$ [mol/l] | Transrepression (TR)(Il-6-Promoter) Efficacy [%] | Transrepression (TR) (Collagenase Promoter) $IC_{50}$ [mol/l] | Transrepression (TR) (Collagenase Promoter) Efficacy [%] |
|---|---|---|---|---|
| Example 2 | $9.2 \times 10^{-10}$ | 66 | $3.7 \times 10^{-9}$ | 92 |
| Example 6 | $1.2 \times 10^{-9}$ | 77 | $2.6 \times 10^{-9}$ | 95 |
| Example 23 | $1.6 \times 10^{-9}$ | 78 | $4.9 \times 10^{-9}$ | 78 |
| Example 29 | $1.5 \times 10^{-9}$ | 79 | $3.4 \times 10^{-9}$ | 105 |
| Pred | $7.8 \times 10^{-9}$ | 94 | $1.0 \times 10^{-8}$ | 96 |
| Dex | $1.5 \times 10^{-9}$ | 100 | $2.2 \times 10^{-9}$ | 100 |

TABLE 6

Transrepression Data

| Compound | Transrepression (TR)(IL-6-Promoter) IC50 [mol/l] | Transrepression (TR)(IL-6-Promoter) Efficacy [%] |
|---|---|---|
| Example 1 | $2.0 \times 10^{-9}$ | 84 |
| Example 2 | $9.2 \times 10^{-10}$ | 66 |
| Example 3 | $5.9 \times 10^{-9}$ | 66 |
| Example 4 | $1.5 \times 10^{-9}$ | 80 |
| Example 14 | $4.2 \times 10^{-9}$ | 85 |
| Example 15 | $1.5 \times 10^{-9}$ | 74 |
| Example 18 | $5.7 \times 10^{-9}$ | 63 |
| Example 19 | $3.8 \times 10^{-9}$ | 91 |
| Example 31 | $5.4 \times 10^{-9}$ | 67 |
| Example 32 | $2.2 \times 10^{-9}$ | 76 |

TABLE 7

Transactivating Data in the Reporter Gene Test

| Compound | Transrepression (TR) (IL-6-Promoter) IC50 [mol/l] | Transrepression (TR) (IL-6-Promoter) Efficacy [%] | Transactivating (TA) (MMTV-Promoter) $EC_{50}$ [mol/l] | Transactivating (TA) (MMTV-Promoter) Efficacy [%] | TA:TR $EC_{50}:IC_{50}$ |
|---|---|---|---|---|---|
| Example 2 | $9.2 \times 10^{-10}$ | 66 | $1.1 \times 10^{-8}$ | 71 | 11.9 |
| Example 8 | $2.8 \times 10^{-9}$ | 67 | $5.0 \times 10^{-8}$ | 25 | 17.8 |
| Example 17 | $4.6 \times 10^{-9}$ | 73 | $4.0 \times 10^{-8}$ | 50 | 8.7 |
| Example 23 | $1.6 \times 10^{-9}$ | 78 | $1.0 \times 10^{-8}$ | 76 | 6.2 |
| Example 29 | $1.5 \times 10^{-9}$ | 79 | $1.3 \times 10^{-8}$ | 59 | 8.7 |
| Example 33 | $2.2 \times 10^{-9}$ | 80 | $4.9 \times 10^{-8}$ | 76 | 22.3 |
| Dex | $1.5 \times 10^{-9}$ | 100 | $7.5 \times 10^{-9}$ | 100 | 5 |

EXAMPLE 14

The antiinflammatory action of the compounds of general formula I were tested in an animal experiment in croton oil-induced inflammation in mice and in rats (J. Exp. Med. (1995), 182, 99–108). In this connection, croton oil in ethanolic solution was administered topically to the animals' ears. The test substances were systemically administered for two hours before the croton oil. After 16–24 hours, the ear weight was measured as a yardstick for the inflammatory edema. To this end, the compounds of formula I show an inflammation that is comparable to the standard (prednisolone) and to some extent a stronger inhibition of the croton oil-induced inflammation (see Table 8).

TABLE 8

Inhibition of Edema Formation in Mice

| Compounds | Edema Inhibition [%] with 3 mg/kg | Edema Inhibition [%] with 30 mg/kg |
|---|---|---|
| Example 2 | 55 | 86 |
| Example 7 | 22 | 75 |
| Example 8 | 33 | 52 |
| Example 29 | 34 | 66 |
| Prednisolone | 35 | 84 |

EXAMPLE 15

As parameters for the side effects of the catabolic metabolism induced by steroids, the activity of the enzyme tyrosinamino transferase (TAT) was determined by photometry from liver homogenates. The activity represents a good yardstick for the undesirable catabolic actions of the glucocorticoids. To measure the TAT induction, the animals (mice and rats) are killed 8 hours after the test substance is administered, the liver is removed, and the TAT activity is measured in the homogenates. In doses in which they have an anti-inflammatory action, the compounds of general formula I do not induce, or induce only to a small extent, the TAT in comparison to steroids (see Table 9).

TABLE 9

Induction of the Tyrosinamino Transferase (TAT) in Mice

| Compounds | Induction Factor* for TAT with 3 mg/kg | Induction Factor for TAT with 30 mg/kg |
|---|---|---|
| Example 23 | 1.1 | 1.0 |
| Example 29 | 1.0 | 2.0 |
| Example 2 | 1.4 | 2.4 |
| Example 7 | 1.2 | 2.4 |
| Prednisolone | 2.6 | 8.0 |

*The induction factor stands for the corresponding n-th increase in enzyme activity of the tyrosinamino transferase in treated animals compared to untreated control animals.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever. Also, any preceding examples can be repeated with similar success by substituting the generically or specifically described reactants and/or operating conditions of this invention for those used in such examples.

Throughout the specification and claims, all temperatures are set forth uncorrected in degrees Celsius and, all parts and percentages are by weight, unless otherwise indicated.

The entire disclosures of all applications, patents and publications, cited herein and of corresponding German application No. 102 61 874.7 filed Dec. 20, 2002, and U.S. Provisional Application Ser. No. 60/438,518, filed Jan. 8, 2003 are incorporated by reference herein.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A compound of formula I

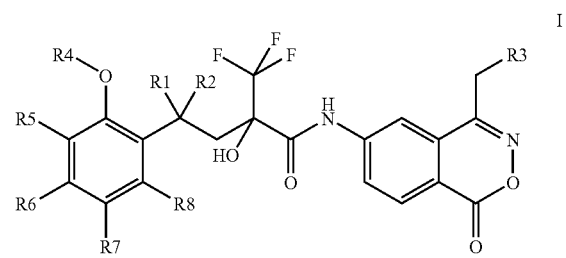

in which
A) $R^1$ and $R^2$ together with the C atom of the chain, stand for a ring with a total of 3–4 links,
$R^3$ stands for a hydrogen atom or a $C_1$–$C_2$-alkyl group,
$R^4$ stands for a hydrogen atom or a $C_1$–$C_2$-alkyl group, and
$R^5$ to $R^8$ are the same or different from one another and stand for a hydrogen atom or a halogen atom,
or
$R^4$ and $R^5$ together stand for a 5-membered heterocyclic ring, which in addition to the oxygen atom optionally can contain another oxygen atom or nitrogen atom;
B) $R^1$ and $R^2$ are the same or different and stand for a $C_1$–$C_2$-alkyl group, or, together with the C atom of the chain, stand for a ring with a total of 3–4 links,
$R^3$ stands for a hydrogen atom or a $C_1$–$C_2$-alkyl group,
$R^6$ to $R^8$ are the same or different from one another and stand for a hydrogen atom or a halogen atom, and
$R^4$ and $R^5$ together stand far a 5-membered heterocyclic ring, which in addition to the oxygen atom optionally can contain another oxygen atom or nitrogen atom;
C) $R^1$ and $R^2$ together with the C atom of the chain, stand for a cyclopropyl ring or a cyclobutyl ring,
$R^3$ stands for a hydrogen atom or a methyl group,
$R^4$ stands for a hydrogen atom or a methyl group, and
$R^5$ to $R^8$ stand for a hydrogen atom and optionally in one or two positions for a fluorine, chlorine, bromine or iodine atom,
or
$R^4$ and $R^5$ together with the inclusion of the phenyl ring atoms 2 and 3 stand for a furan ring, a dihydrofuran ring, a 1,3-dioxole ring or a 1,3-oxazole ring, and
$R^6$, $R^7$ and $R^8$ mean a hydrogen atom and optionally fluorine, chlorine, bromine or iodine atoms in one or two positions,
or
D) $R^1$ and $R^2$ are the same or different and stand for a methyl group or wi ethyl group, or together with the C atom of the chain, stand for a cyclopropyl ring or a cycloburyl ring, $R^3$ stands for a hydrogen atom or a methyl group, $R^4$ and $R^5$ together with the inclusion of the phenyl ring atoms 2 and 3 stand for a furan ring, a dihydrofuran ring, a 1,3-dioxole ring or a 1,3-oxazole ring, and $R^6$, $R^7$ and $R^8$ mean a hydrogen atom and optionally fluorine, chlorine, bromine or iodine atoms in one or two positions, which compound of formula I can be in its enantiomeric form or its racemic form.

2. A compound of formula I

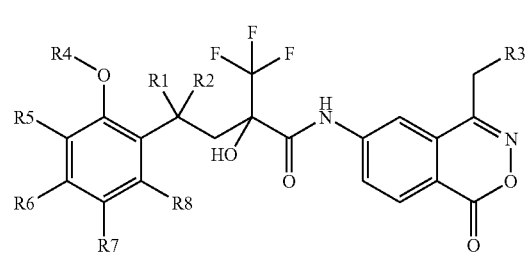

in which

| $R^1/R^2$ | $R^4$–$R^8$ | $R^3$ |
|---|---|---|
| CH$_3$, CH$_3$ | R4–R5 = —CH$_2$—O— | H |
| CH$_3$, CH$_3$ | R4–R5 = —CH$_2$—O— | H |
| —(CH$_2$)$_2$— | R4–R5 = —CH$_2$—O— | H |
| —(CH$_2$)$_2$— | R4–R5 = —CH$_2$—O— | H |
| —(CH$_2$)$_3$— | R4–R5 = —CH$_2$—O— | H |
| —(CH$_2$)$_3$— | R4–R5 = —CH$_2$—O— | H |
| CH$_3$, CH$_3$ | R4–R5 = —CH=CH— | CH$_3$ |
| CH$_3$, CH$_3$ | R4–R5 = —CH=N—, R6 = F | H |
| —(CH$_2$)$_2$— | R4 = CH$_3$, R5 = F | H |
| CH$_3$, CH$_3$ | R4–R5 = —CH$_2$—O— | CH$_3$ |
| —(CH$_2$)$_2$— | R4–R5 = —CH$_2$—CH$_2$— | H |
| —(CH$_2$)$_2$— | R4–R5 = —CH$_2$—CH$_2$— | H |
| —(CH$_2$)$_3$— | R4–R5 = —CH$_2$—CH$_2$— | H |
| —(CH$_2$)$_3$— | R4–R5 = —CH$_2$—CH$_2$— | H |
| —(CH$_2$)$_3$— | R4–R5 = —CH$_2$—CH$_2$— | CH$_3$ |
| —(CH$_2$)$_3$— | R4–R5 = —CH$_2$—CH$_2$— | CH$_3$ |
| CH$_3$, CH$_3$ | R7 = F, R4–R5 = —CH$_2$—O— | H |
| CH$_3$, CH$_3$ | R7 = F, R4–R5 = —CH$_2$—O— | H |
| CH$_3$, CH$_3$ | R6 = Br, R4–R5 = —CH$_2$—O— | H |
| —(CH$_2$)$_2$— | R4 = CH$_3$, R6 = I | H |
| CH$_3$, CH$_3$ | R4–R5 = —CH=CH— | H |
| (CH$_2$)$_3$ | R4–R5 = —CH=CH— | H |
| —(CH$_2$)$_2$— |  | H |
| —(CH$_2$)$_3$— | R4–R5 = —CH=N—, R6 = F | H |
| —(CH$_2$)$_3$— | R4–R5 = —CH=N—, R6 = F | H |
| —(CH$_2$)$_3$— | R7 = F | H |
| —(CH$_2$)$_3$— | R7 = F | H |
| —(CH$_2$)$_2$— | R5 = F | H |
| —(CH$_2$)$_3$— | R4 = CH$_3$, R5 = F | H |
| —(CH$_2$)$_3$— | R4 = CH$_3$, R5 = F | H |
| —(CH$_2$)$_3$— | R5 = F | H |
| CH$_3$, CH$_2$CH$_3$ | R5 = F | H | wherein any radicals $R^4$ to $R^8$ that are nor otherwise indicated mean hydrogen.

3. A pharmaceutical composition comprising a compound according to claim 1 and a pharmaceutically compatible vehicle.

4. A method for the treatment of a rheumatic disease, degenerative joint disease, allergy, vascular inflammation (vasculitis), graft-versus-host disease, severe shock condition, vomiting or pain with inflarnniatory origins comprising administering a patient in need thereof an effective amount of a pharmaceutical composition according to claim 3.

5. A pharmaceutical composition comprising a compound according to claim 2 and a pharmaceutically compatible vehicle.

6. A method for the treatment of a rheumatic disease, degenerative joint disease, allergy, vascular inflammation (vasculitis), graft-versus-host disease, severe shock condition, vomiting or pain with inflammatory origins comprising administering a patient in need thereof an effective amount of a pharmaceutical composition according to claim 5.

7. A compound according to claim 1 in which $R^1$ and $R^2$ together with the C atom of the chain, stand for a ring with a total of 3–4 links, $R^3$ stands for a hydrogen atom or a $C_1$–$C_2$-alkyl group, $R^4$ stands for a hydrogen atom or a $C_1$–$C_2$-alkyl group, and $R^5$ to $R^8$ are the same or different from one another and stand for a hydrogen atom or a halogen atom, or $R^4$ and $R^5$ together stand for a 5-membered heterocyclic ring, which in addition to the oxygen atom optionally can contain another oxygen atom or nitrogen atom.

8. A compound according to claim 1 in which $R^1$ and $R^2$ are the same or different and stand for a $C_1$–$C_2$-alkyl group, or, together with the C atom of the chain, stand for a ring with a total of 3–4 links, $R^3$ stands for a hydrogen atom or a $C_1$–$C_2$-alkyl group, $R^6$ to $R^8$ are the same or different from one another and stand for a hydrogen atom or a halogen atom, and $R^4$ and $R^5$ together stand for a 5-membered heterocyclic ring, which in addition to the oxygen atom optionally can contain another oxygen atom or nitrogen atom.

9. A compound according to claim 1, in which $R^1$ and $R^2$ together with the C atom of the chain, stand for a cyclopropyl ring or a cyolobutyl ring, $R^3$ stands for a hydrogen atom or a methyl group, $R^4$ stands for a hydrogen atom or a methyl group, and $R^5$ to $R^8$ stand for a hydrogen atom and optionally in one or two positions for a fluorine, chlorine, bromine or iodine atom, or $R^4$ and $R^5$ together with the inclusion of the phenyl ring atoms 2 and 3 stand for a furan ring, a dihydrofuran ring, a 1,3-dioxole ring or a 1,3-oxazole ring, and $R^6$, $R^7$ and $R^8$ mean a hydrogen atom and optionally fluorine, chlorine, bromine or iodine atoms in one or two positions.

10. A compound according to claim 1, in which $R^1$ and $R^2$ are the same or different and stand for a methyl group or an ethyl group, or together with the C atom of the chain, stand for a cyclopropyl ring or a cyclobutyl ring, $R^3$ stands for a hydrogen atom or a methyl group, $R^4$ and $R^5$ together with the inclusion of the phenyl ring atoms 2 and 3 stand for a furan ring, a dihydrofuran ring, a 1,3-dioxole ring or a 1,3-oxazole ring, and $R^6$, $R^7$ and $R^8$ mean a hydrogen atom and optionally fluorine, chlorine, bromine or iodine atoms in one or two positions.

11. A compound according to claim 2 in which

| R$^1$ / R$^2$ | R$^4$–R$^8$ | R$^3$ |
|---|---|---|
| CH$_3$, CH$_3$ | R4–R5 = —CH$_2$—O— | H |
| CH$_3$, CH$_3$ | R4–R5 = —CH$_2$—O— | H |
| —(CH$_2$)$_2$— | R4–R5 = —CH$_2$—O— | H |
| —(CH$_2$)$_2$— | R4–R5 = —CH$_2$—O— | H |
| —(CH$_2$)$_3$— | R4–R5 = —CH$_2$—O— | H |
| —(CH$_2$)$_3$— | R4–R5 = —CH$_2$—O— | H |
| CH$_3$, CH$_3$ | R4–R5 = —CH=CH— | CH$_3$ |
| CH$_3$, CH$_3$ | R4–R5 = —CH=N—, R6 = F | H |
| —(CH$_2$)$_2$— | R4 = CH$_3$, R5 = F | H |
| CH$_3$, CH$_3$ | R4–R5 = —CH$_2$—O— | CH$_3$ |
| —(CH$_2$)$_2$— | R4–R5 = —CH$_2$—CH$_2$— | H |
| —(CH$_2$)$_2$— | R4–R5 = —CH$_2$—CH$_2$— | H |
| —(CH$_2$)$_3$— | R4–R5 = —CH$_2$—CH$_2$— | H |
| —(CH$_2$)$_3$— | R4–R5 = —CH$_2$—CH$_2$— | H |
| —(CH$_2$)$_3$— | R4–R5 = —CH$_2$—CH$_2$— | CH$_3$ |
| —(CH$_2$)$_3$— | R4–R5 = —CH$_2$—CH$_2$— | CH$_3$ |
| CH$_3$, CH$_3$ | R7 = F, R4–R5 = —CH$_2$—O— | H |
| CH$_3$, CH$_3$ | R7 = F, R4–R5 = —CH$_2$—O— | H |
| CH$_3$, CH$_3$ | R6 = Br, R4–R5 = —CH$_2$—O— | H |
| —(CH$_2$)$_2$— | R4 = CH$_3$, R6 = I | H |
| CH$_3$, CH$_3$ | R4–R5 = —CH=CH— | H |
| (CH$_2$)$_3$ | R4–R5 = —CH=CH— | H |
| —(CH$_2$)$_2$— | | H |
| —(CH$_2$)$_3$— | R4–R5 = —CH=N—, R6 = F | H |
| —(CH$_2$)$_3$— | R4–R5 = —CH=N—, R6 = F | H |
| —(CH$_2$)$_3$— | R7 = F | H |
| —(CH$_2$)$_3$— | R7 = F | H |
| —(CH$_2$)$_2$— | R5 = F | H |
| —(CH$_2$)$_3$— | R4 = CH$_3$, R5 = F | H |
| —(CH$_2$)$_3$— | R4 = CH$_3$, R5 = F | H |
| —(CH$_2$)$_3$— | R5 = F | H | wherein any radicals R$^4$ to R$^8$ that are not otherwise indicated mean hydrogen.

12. A compound according to claim 1, which is in its enantiomeric form.

13. A compound according to claim 1, which is in its racemic form.

14. A compound according to claim 2, which is in its enantiomeric or racemic form.

15. A pharmaceutical composition comprising a compound according to claim 7 and a pharmaceutically compatible vehicle.

16. A pharmaceutical composition comprising a compound according to claim 8 and a pharmaceutically compatible vehicle.

17. A compound of formula I

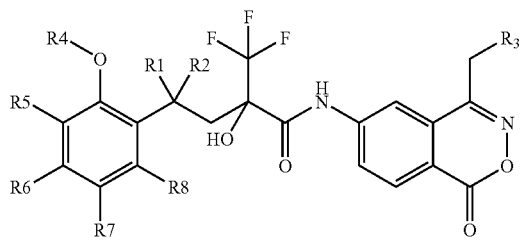

in which

| R$^1$ / R$^2$ | R$^4$–R$^8$ | R$^3$ | Isomerism |
|---|---|---|---|
| CH$_3$, CH$_3$ | R4–R5 = —CH$_2$—O— | H | Racemate |
| CH$_3$, CH$_3$ | R4–R5 = —CH$_2$—O— | H | (+)-Enantiomer |
| —(CH$_2$)$_2$— | R4–R5 = —CH$_2$—O— | H | Racemate |
| —(CH$_2$)$_2$— | R4–R5 = —CH$_2$—O— | H | (+)-Enantiomer |
| —(CH$_2$)$_3$— | R4–R5 = —CH$_2$—O— | H | Racemate |
| —(CH$_2$)$_3$— | R4–R5 = —CH$_2$—O— | H | (+)-Enantiomer |
| CH$_3$, CH$_3$ | R4–R5 = —CH=CH— | CH$_3$ | (+)-Enantiomer |
| CH$_3$, CH$_3$ | R4–R5 = —CH=N—, R6 = F | H | (+)-Enantiomer |
| —(CH$_2$)$_2$— | R4 = CH$_3$, R5 = F | H | (+)-Enantiomer |
| CH$_3$, CH$_3$ | R4–R5 = —CH$_2$—O— | CH$_3$ | (+)-Enantiomer |
| —(CH$_2$)$_2$— | R4–R5 = —CH$_2$—CH$_2$— | H | Racemate |
| —(CH$_2$)$_2$— | R4–R5 = —CH$_2$—CH$_2$— | H | (+)-Enantiomer |
| —(CH$_2$)$_3$— | R4–R5 = —CH$_2$—CH$_2$— | H | Racemate |
| —(CH$_2$)$_3$— | R4–R5 = —CH$_2$—CH$_2$— | H | (+)-Enantiomer |
| —(CH$_2$)$_3$— | R4–R5 = —CH$_2$—CH$_2$— | CH$_3$ | Racemate |
| —(CH$_2$)$_3$— | R4–R5 = —CH$_2$—CH$_2$— | CH$_3$ | (+)-Enantiomer |
| CH$_3$, CH$_3$ | R7 = F, R4–R5 = —CH$_2$—O— | H | Racemate |
| CH$_3$, CH$_3$ | R7 = F, R4–R5 = —CH$_2$—O— | H | (+)-Enantiomer |
| CH$_3$, CH$_3$ | R6 = Br, R4–R5 = —CH$_2$—O— | H | (+)-Enantiomer |
| —(CH$_2$)$_2$— | R4 = CH$_3$, R6 = I | H | (+)-Enantiomer |
| CH$_3$, CH$_3$ | R4–R5 = —CH=CH— | H | (+)-Enantiomer |
| (CH$_2$)$_3$ | R4–R5 = —CH=CH— | H | (+)-Enantiomer |
| —(CH$_2$)$_2$— | | H | (+)-Enantiomer |
| —(CH$_2$)$_3$— | R4–R5 = —CH=N—, R6 = F | H | Racemate |
| —(CH$_2$)$_3$— | R4–R5 = —CH=N—, R6 = F | H | (+)-Enantiomer |
| —(CH$_2$)$_3$— | R7 = F | H | Racemate |
| —(CH$_2$)$_3$— | R7 = F | H | (+)-Enantiomer |
| —(CH$_2$)$_2$— | R5 = F | H | (+)-Enantiomer |
| —(CH$_2$)$_3$— | R4 = CH$_3$, R5 = F | H | Racemate |
| —(CH$_2$)$_3$— | R4 = CH$_3$, R5 = F | H | (+)-Enantiomer |
| —(CH$_2$)$_3$— | R5 = F | H | (+)-Enantiomer |
| CH$_3$, CH$_2$CH$_3$ | R5 = F | H | (+)-Enantiomer | wherein any radicals R$^4$ to R$^8$ that are nor otherwise indicated mean hydrogen.

18. A pharmaceutical composition comprising a compound according to claim 17 and a pharmaceutically compatible vehicle.

19. A method for the treatment of a rheumatic disease, degenerative joint disease, allergy, vascular inflammation (vasculitis), graft-versus-host disease, severe shock condition, vomiting or pain with inflammatory origins comprising administering a patient in need thereof an effective amount of a pharmaceutical composition according to claim 18.

* * * * *

UNITED STATES PATENT AND TRADEMARK OFFICE
CERTIFICATE OF CORRECTION

PATENT NO. : 7,112,584 B2 Page 1 of 1
APPLICATION NO. : 10/739407
DATED : September 26, 2006
INVENTOR(S) : Stefan Jaroch It is certified that error appears in the above-identified patent and that said Letters Patent is hereby corrected as shown below:

Column 28, line 47 reads "far" should read --for --

Column 28, line 65 reads "wi" should read -- an --

Signed and Sealed this

Twenty-second Day of May, 2007

JON W. DUDAS
*Director of the United States Patent and Trademark Office*